(12) United States Patent
Wanders

(10) Patent No.: US 9,668,854 B2
(45) Date of Patent: Jun. 6, 2017

(54) OPHTHALMIC LENS HAVING ENHANCED OPTICAL BLENDING ZONE

(75) Inventor: Bernardus Franciscus Maria Wanders, Angerlo (NL)

(73) Assignee: OCULENTIS HOLDING B.V., Eerbeek (NL)

( * ) Notice: Subject to any disclaimer, the term of this patent is extended or adjusted under 35 U.S.C. 154(b) by 481 days.

(21) Appl. No.: 14/001,934

(22) PCT Filed: Feb. 27, 2012

(86) PCT No.: PCT/NL2012/050115
§ 371 (c)(1),
(2), (4) Date: Nov. 5, 2013

(87) PCT Pub. No.: WO2012/118371
PCT Pub. Date: Sep. 7, 2012

(65) Prior Publication Data
US 2014/0067060 A1 Mar. 6, 2014

Related U.S. Application Data

(60) Provisional application No. 61/490,703, filed on May 27, 2011.

(30) Foreign Application Priority Data

Feb. 28, 2011 (NL) ..................................... 2006307

(51) Int. Cl.
*A61F 2/16* (2006.01)
(52) U.S. Cl.
CPC .................................. *A61F 2/1618* (2013.01)
(58) Field of Classification Search
CPC .... A61F 2/1613; A61F 2/1618; A61F 2/1654; A61F 2/1648; G02C 7/044
See application file for complete search history.

(56) References Cited

U.S. PATENT DOCUMENTS

| 4,010,496 A | 3/1977 | Neefe |
| 4,693,572 A | 9/1987 | Tseutaki |

(Continued)

FOREIGN PATENT DOCUMENTS

| EP | 2 219 065 | * 8/2010 |
| WO | 02074210 A2 | 9/2002 |

(Continued)

OTHER PUBLICATIONS

Bruckner; Ocular Surgery News, vol. 10, No. 11, Jun. 1, 1992.

*Primary Examiner* — David H Willse
*Assistant Examiner* — Tiffany Shipmon
(74) *Attorney, Agent, or Firm* — Porzio Bromberg Newman P.C.

(57) ABSTRACT

An intraocular lens with a lens comprises a main lens part having a main lens surface and a main optical axis defining radial, tangential and axial directions; and a recessed part having a recess surface and extending between said main optical axis and a circumference of said lens, the recessed part comprising a secondary lens part with a secondary lens surface having a positive relative optical power with respect to an optical power of said main lens surface. The main lens surface extends in an outward radial direction towards a main lens outer circumference section remote from said the optical axis. The main lens outer circumference section and the main lens surface define an imaginary main lens outer circumference section that would have at least partially provided a main lens outer circumference together with the main lens outer circumference section in case the recessed part would have been absent; and an imaginary main lens surface section that would have been part of the main lens surface in case said recessed part would have been absent, the recess surface being recessed with respect to the imaginary main lens surface section. The recessed part extends in an outward radial direction to an outer recess boundary (Continued)

Figure 1:
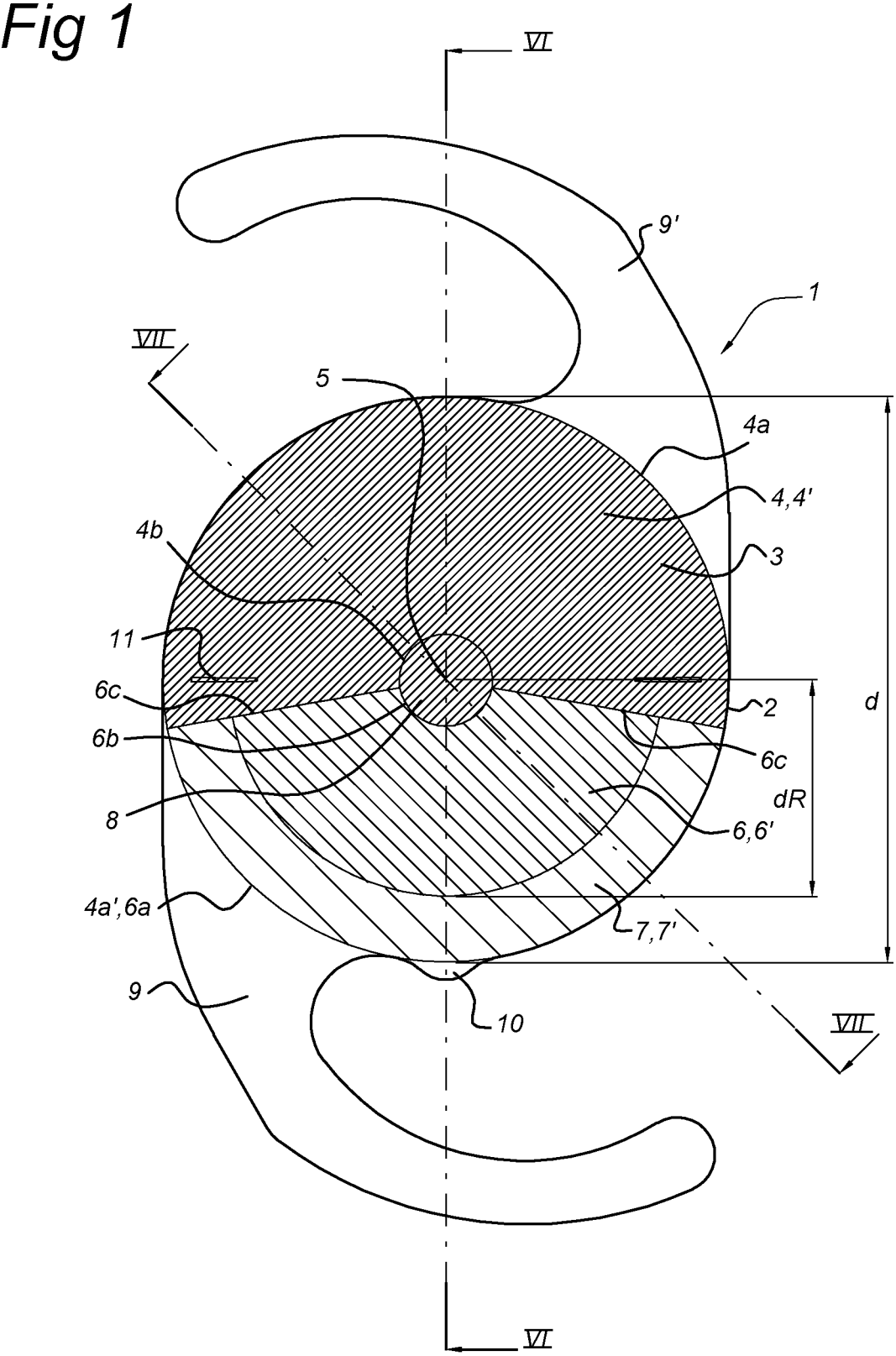

remote from said main optical axis, the outer recess boundary extending along or beyond said imaginary main lens outer circumference section as seen in an outward radial direction.

14 Claims, 19 Drawing Sheets

(56) References Cited

U.S. PATENT DOCUMENTS

| | | |
|---|---|---|
| 5,236,452 A | 8/1993 | Nordan |
| 5,589,024 A | 12/1996 | Blake |
| 6,409,339 B1 | 6/2002 | Wanders |
| 2003/0055498 A1 | 3/2003 | Paul |
| 2010/0036490 A1 | 2/2010 | Deacon |

FOREIGN PATENT DOCUMENTS

| | | |
|---|---|---|
| WO | 2005055875 A2 | 6/2005 |
| WO | 2010/095938 | 8/2010 |
| WO | 2010095938 A1 | 8/2010 |
| WO | 2010147455 A1 | 12/2010 |

\* cited by examiner

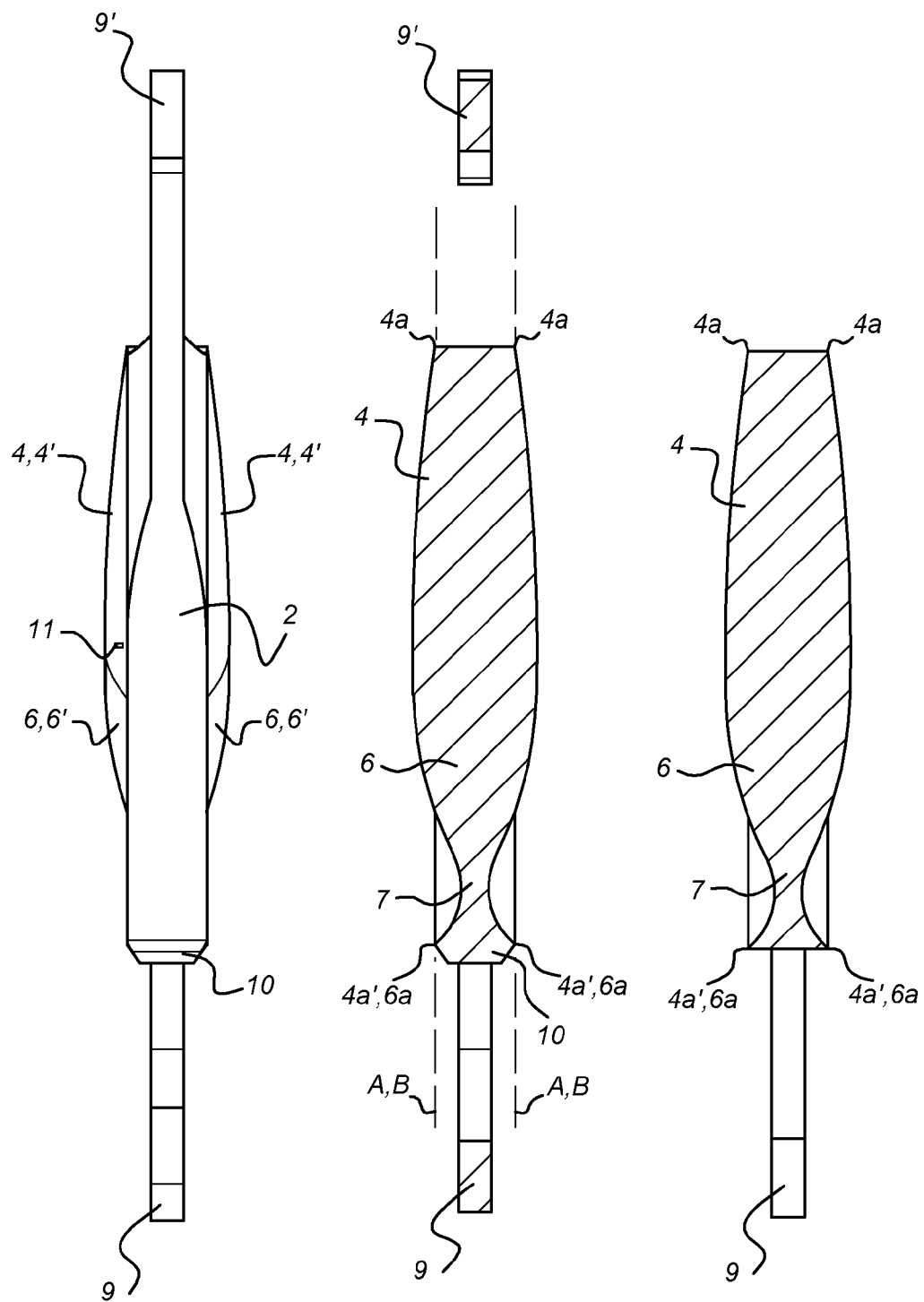

OPHTHALMIC LENS HAVING ENHANCED OPTICAL BLENDING ZONE

CROSS REFERENCE TO RELATED APPLICATION

This is a National Stage of International Application No. PCT/NL2012/050115, filed Feb. 27, 2012, which claims the benefit of Application No. 2006307, filed in The Netherlands on Feb. 28, 2011, and Application No. 61/490,703 filed in the United States of American on May 27, 2011, the disclosures of which Applications are incorporated by reference herein.

BACKGROUND

The present invention relates to an intraocular lens having a lens with a main lens part and a recessed part.

Such a lens with a distance part and a near part is described in EP 0 858 613 A, U.S. Pat. No. 6,409,339 and EP 2 219 065 A from the current inventor, and which are incorporated by reference as if fully set forth. These documents disclose contact lenses, but also refer to intraocular lenses, IOL's. A lens of this type differs from other lenses in that the reading part is located within the (imaginary) boundary of the distance part. That is to say the reading part is on or within the imaginary radius of the outer boundary of the distance part. If a partial part is used this is preferably made as a sector which extends from the centre of the lens. A reading part is thus recessed with respect to a distance part. This lens proved to have many possibilities. There is, however, room for further improvement. One of the problems of the known intraocular lenses is the occurrence of halo's and other visual artefacts that can occur at various light conditions, especially under low light conditions.

SUMMARY OF THE INVENTION

The invention aims to improve the known intra ocular lenses.

Yet another or alternative object of the invention is to provide an intraocular lens with reduced visual artefacts, also at varying light conditions.

To that end, the invention provides an intraocular lens having a lens comprising a main lens part having a main lens surface and a main optical axis defining radial, tangential and axial directions; and a recessed part having a recess surface and extending between said main optical axis and a circumference of said lens, said recessed part comprising a secondary lens part with a secondary lens surface having a positive relative optical power with respect to an optical power of said main lens surface, said main lens surface extending in an outward radial direction towards a main lens outer circumference section remote from said main optical axis, said main lens outer circumference section and said main lens surface defining an imaginary main lens outer circumference section that would have at least partially provided a main lens outer circumference together with said main lens outer circumference section in case said recessed part would have been absent; and an imaginary main lens surface section that would have been part of said main lens surface in case said recessed part would have been absent, said recess surface being recessed with respect to said imaginary main lens surface section, wherein said recessed part extends in an outward radial direction to an outer recess boundary remote from said main optical axis, said outer recess boundary extending along or beyond said imaginary main lens outer circumference section as seen in an outward radial direction.

In an embodiment said outer recess boundary is at a distance from said main optical axis which is equal to or larger than a distance of said imaginary main lens outer circumference section from said main optical axis in a same radial direction.

In a further embodiment said imaginary main lens outer circumference section and said imaginary main lens surface are essentially defined by mirror symmetry with respect to a mirror plane comprising said main optical axis, said imaginary main lens outer circumference section and said imaginary main lens surface on one side of said mirror plane essentially coinciding with mirror images of part of said main lens outer circumference section and part of said main lens surface, respectively, on the other side of said mirror plane; and/or said imaginary main lens outer circumference section and said imaginary main lens surface are essentially defined by line symmetry with respect to said main optical axis, said imaginary main lens outer circumference section and said imaginary main lens surface on one side of said main optical axis essentially coinciding with mirror images of part of said main lens outer circumference section and part of said main lens surface, respectively, on the other side of said main optical axis.

The intraocular lens according to the invention was found to reduce one or more night time visual symptoms such as halos and glare or flare related to an intra ocular lens comprising a main lens part and a recessed part. It has been found after extensive clinical testing that for some patients, reflections and halo's occurred when implanting known IOL's. Research showed that for an MIOL as disclosed in U.S. Pat. No. 6,409,339 and EP 2 219 065 A, the transition profile that is used to bridge the step height between the sector lower boundary of the recessed part is not optimal. It could result in blurred vision, reflexions, halo's and glare, in particular for persons with a large pupil size, in particular under mesopic light conditions. Especially, these patients or users can have impaired vision in some circumstances at night for instance when driving a car. These problems can be caused by a combination of light from incoming head lights and big pupil size in the dark. The optic configuration as disclosed herein provides a solution to minimize these optical side effects such as halos and glare halo's which were found to occur with big pupil size, and at the same time provide a clear vision with high contrast at near and intermediate distance. Tests showed that in low light conditions, there are persons having an extremely large pupil. For these persons, the end of the recessed part can cause disturbances. In order to overcome that problem, the inventor basically designed the three related solutions.

In yet a further embodiment said imaginary main lens outer circumference section is at least essentially in a first plane perpendicular to said main optical axis, and said outer recess boundary is at least essentially in a second plane perpendicular to said main optical axis, said first plane at least essentially coinciding with said second plane.

In yet a further embodiment said outer recess boundary at least essentially coincides with said imaginary main lens outer circumference section.

In yet a further embodiment said imaginary main lens outer circumference section is at least essentially in a first plane perpendicular to said main optical axis, and said outer recess boundary is at least essentially in a second plane perpendicular to said main optical axis, said first plane being at a distance from said second plane as seen in an axial direction outward of said lens.

In yet a further embodiment said imaginary main lens outer circumference section is at a distance from said outer recess boundary as seen in an axial direction outward of said lens.

In yet a further embodiment said recess surface essentially only comprises said secondary lens surface extending to said outer recess boundary.

In yet a further embodiment said recess surface essentially only comprises an essentially concave surface section extending along said outer recess boundary, and said secondary lens surface extending to said essentially concave surface section. In an embodiment said concave surface section extends between about 0.2 and 1.2 mm in the radial direction.

In yet a further embodiment said recessed part in tangential directions is bounded by meridian boundaries extending along meridians of said main lens surface passing through said main optical axis. In an embodiment said recessed part extends between 160 and 190 degrees in said tangential directions between said meridian boundaries.

In yet a further embodiment said main lens outer circumference at least essentially coincides with said circumference of said lens.

The concave region of the sagital region in one embodiment provides a region which is divergent with respect to the optical axis. Furthermore, it allows the thickness of the IOL at the edge of the lens to increase in order to provide an edge which is thick enough to give sufficient rigidity and material strength to the IOL. In the raised lens embodiment, the peripheral blending zone is avoided by raising the entire lens to such an extend that the radial end or peripheral zone of the recessed part determines the lens diameter, or the entire lens is raised even more to increase the rigidity of the IOL.

In yet a further embodiment said secondary lens surface comprises at least two secondary lens surface sections neighbouring in a radial direction, an optical power of one secondary lens surface section being larger in an outward radial direction with respect to a neighbouring secondary lens surface section.

In yet a further embodiment said lens further comprises a central lens part around said main optical axis, said central lens part fitting within a circle around said main optical axis and having a diameter between 0.1 and 2.0 mm. In an embodiment a surface of said central part is adjacent to said main lens surface, defining a main lens inner circumference section of said main lens surface, and adjacent to said recess surface, defining an inner recess boundary of said recess surface.

In yet a further embodiment said main lens part is configured for optimizing distance vision of a person provided with said intraocular lens. In a yet further embodiment said secondary lens part is configured for optimizing near and/or intermediate vision of a person provided with said intraocular lens. In a yet further embodiment said main lens part has an optical power between about −20 and +35 dioptre. In a yet further embodiment said secondary lens surface has a relative optical power between +0.5 and 10.0 with respect to said main lens surface.

In yet a further embodiment said main lens outer circumference fits within a circle around said main optical axis and having a diameter between 5 and 7 mm.

In yet a further embodiment said intraocular lens comprising a posterior side for facing towards the posterior chamber of the human eye, and an anterior side for facing away from the posterior chamber when positioned in the human eye, said anterior side and/or said posterior side being configured according to any one of the previous embodiments.

In the last embodiment, the lens is split and distributed over the front side and the back of the IOL. In that way, the radii of curvature of both the main lens part as well as of the recessed part can be reduced. Thus, the steepness and width of the blending zones can be reduced.

The various embodiments can be combined in order to achieve even better IOL's, for instance, allowing a higher relative dioptre of the recessed part.

An IOL is often used in order to replace the normal eye lens, for instance in case of cataract. The main optics of the lens of the IOL is designed in such a way to provide vision which as close as possible resembles the vision of an emmetropic eye. The lens in fact is an ophthalmic lens. The lens of the IOL often is a part of an almost perfect sphere. In practise, however, the main lens part and/or the recessed part can also be designed to additionally compensate for astigmatism, spherical aberration or other higher order aberrations. To that end, the lens can additionally have a aspirical, cylindrical and/or toroidal surface, or can have another optical design. Such an additional curvature of the lens makes the circumference of the lens for instance elliptic or causes it to have another non-circular circumference. For the discussion and the features of the current invention, such an "unroundness" will be considered as "essentially round". In the claims and the description, it can be referred to as "essentially round" or "essentially circular". In order to provide a clear definition of the diameter of a lens that can have a circumference that can also be more or less elliptic, the diameter is defined as that of "a circle in which the circumference fits". Such a circle will thus have its center at the optical axis and has the diameter of the largest cross section of the lens.

Again, when discussing the surfaces of the various lens parts, it is evident that these usually are almost the shape of sphere parts. Thus, when following the surface "in a radial direction", in fact the trajectory of a meridian on a sphere is followed. Furthermore, it should be evident that the radially remote part of the recessed part, also referred to as its peripheral part, can also be aspheric, cylindrical or toriodal in addition to its spherical curvature. In practise, the height difference between the surface of the recessed part at the peripheral end and the radially adjacent surface of the rest of the IOL may be less than 50 microns. For instance, in such a case, the surface of the central part of the recessed part can match the lens plane, while along the circumference in circumferential or tangential direction, i.e. about 60 or more degrees remote from the central part of the recessed part, the recessed part can be less than 50 microns below that lens plane. In order to provide an easy design, the main lens part can continue on the haptic.

In fact, the surface of the recessed part at the circumference in respect to the current discussion functionally matches any further surface of the IOL, or functionally matches the lens plane, if a remaining height difference is less than 10% of the largest height difference of the surface of the recessed part and the imaginary main lens surface at that position. In other words, at the deepest point of the recessed part. Usually, this height difference is less than 50 microns. The height difference can be below 10 microns.

In an embodiment said circle of said lens has a diameter of about 5-7 mm. In particular, the diameter is between 5.5 and 6.5 mm. Such a diameter is found to be a good trade off between optical performance and maximum pupil size.

In an embodiment said recessed part in radial direction has different dioptre value zones, in an embodiment the recessed part has a first sector closest to the optical axis having a dioptre between +1.00 en +5.00, in an embodiment between +0.5 and +10.0, relative to said main lens part, and a second sector matching said first sector and starting from between 1.5 and 2.4 mm in radial direction, in particular between 1.60 and 2.00 mm from the optical axis and continuing to the lens circumference and having a dioptre functionally the same as the dioptre of said main lens part.

In another embodiment of the first embodiment of the IOL, said recessed part in radial direction has different dioptre values zones. In an embodiment, the recessed part has a first sector closest to the optical axis having a first dioptre that is larger than the dioptre of the main lens part and extending in radial direction and a further sector, matching the first sector and having a dioptre that is larger than the dioptre of the first sector.

In an embodiment the recessed part has a first sector with a relative dioptre of +1.00-+4.00 with respect to the main lens part. In a further embodiment, the first sector of the recessed part has a width in radial direction of 0.1-1.5 mm. In a further embodiment, the recessed part has a second sector matching the first sector at its perimeter and which has a relative dioptre of +1.00-+5.00, in an embodiment between +1.0 and +10.0, with respect to the main lens part. In an embodiment, the second sector has a width in radial direction of 1.2-2.6 mm. In yet a further embodiment, the recessed part has a third sector, matching the second sector at its perimeter and which has a relative dioptre differing less than 0.5 from the main lens part. In an embodiment, the second sector extends up to the circumference. The total recessed part in an embodiment extends between 1.5-3.5 mm from the optical axis.

In another embodiment said recessed part in radial direction has different dioptre values zones, in an embodiment the recessed part has a first sector having a first dioptre that is larger than the dioptre of the main lens part and extending in radial direction and a second sector, matching the first sector and having a dioptre that is larger than the dioptre of the first sector and a further sector, matching the second sector and having a dioptre equal to the main part. It can for instance be within 0.5 Dioptre equal to the main part.

In an embodiment said recessed part in radial direction connects to said concave part continuously.

In an embodiment said recessed part in radial direction connects to said further part discontinuously. In other words, the matching surfaces match, but in radial direction the first derivative of the curvature of the surface is not continuous. Surprisingly, it was found that this does not result in visually unpleasant effects.

In an embodiment the surface of said main lens at said circumference is essentially in a lens plane, and in a radial direction the surface of said recessed part runs essentially up to or below said lens plane, after which a radius of curvature of the surface continuously decreases, the surface subsequently becomes concave and while continuing in radial direction the surface of the recessed part approaches the lens plane again at or near the circumference.

In an embodiment said recessed part in radial direction has a width of about 1.6-3.5 mm and said concave part extends about 0.1 en 1.2 mm in radial direction.

In an embodiment said recessed part extends from said central part.

In an embodiment said recessed parts each extend between said optical axis and said circumference.

In an embodiment said recessed part of the front and said recessed part on the back together have a relative dioptre of about +3.0 to about +12 with respect to the combined optical power of said main lens part on the front and the back of the IOL.

The invention further pertains to an apparatus comprising one or more of the characterising features described in the description and/or shown in the attached drawings. The invention further pertains to a method comprising one or more of the characterising features described in the description and/or shown in the attached drawings.

The various aspects discussed in this patent can be combined in order to provide additional advantages. Furthermore, some of the features can form the basis for one or more divisional applications.

DESCRIPTION OF EMBODIMENTS WITH REFERENCE TO THE DRAWINGS

Several embodiments of a Multifocal Sector Ophthalmic Lens, (MSOL) are shown in the attached drawings, in which like or same reference symbols indicate like or same parts, showing in:

FIGS. 1-7 several views of an MSIOL with a concave region, with

Figure 2:
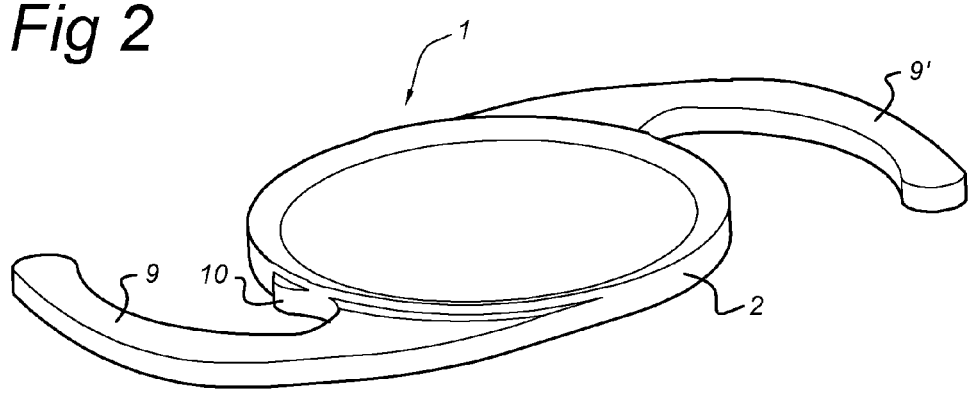
Figure 3:
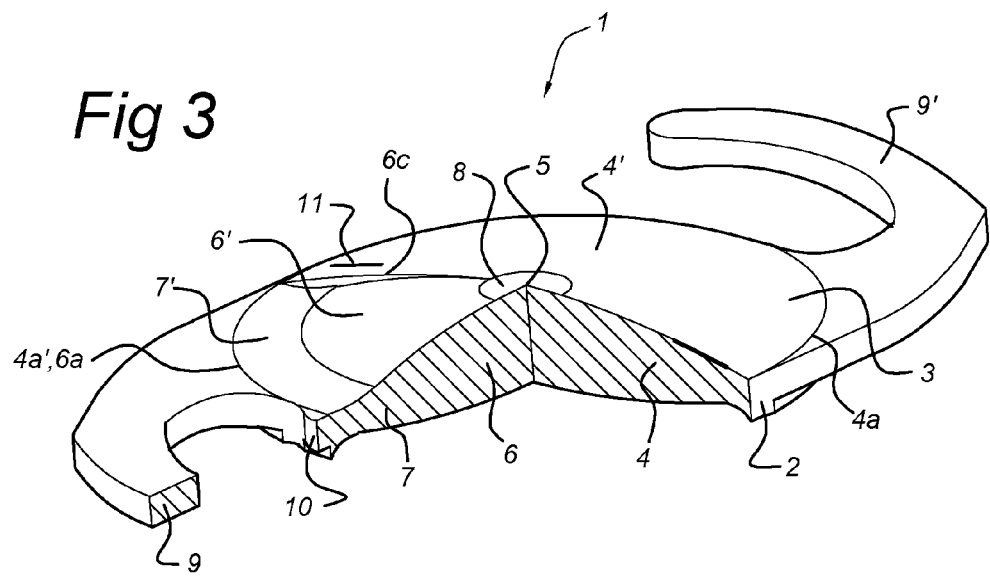
Figure 4:
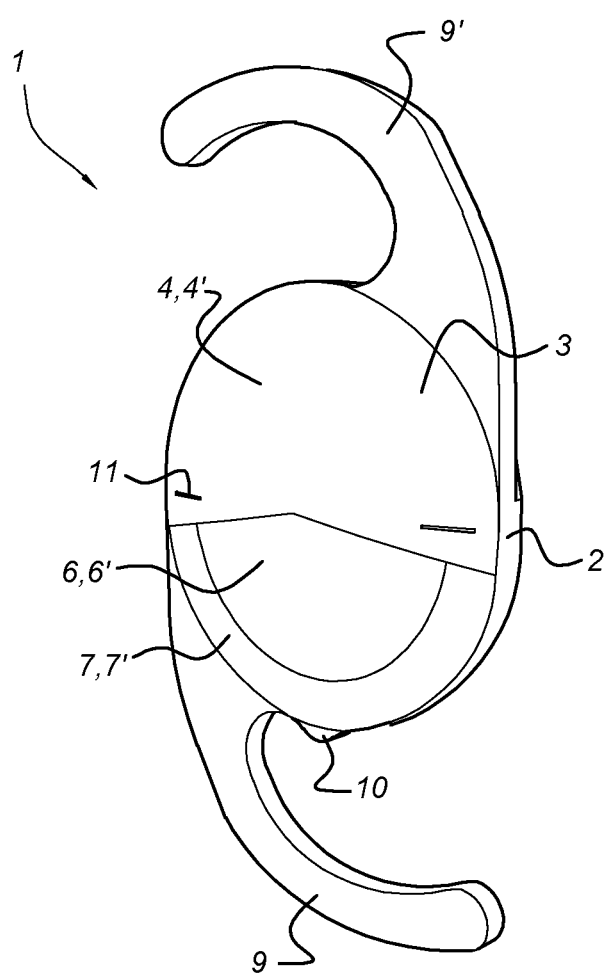
Figure 5:
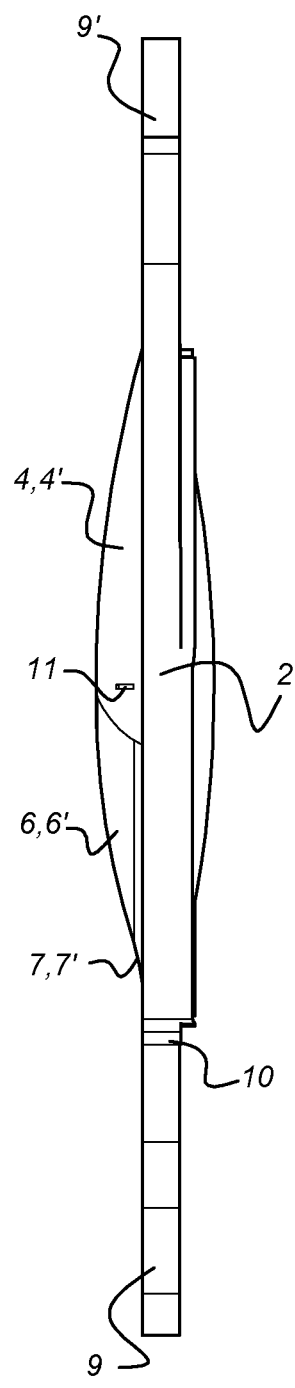
Figure 6:
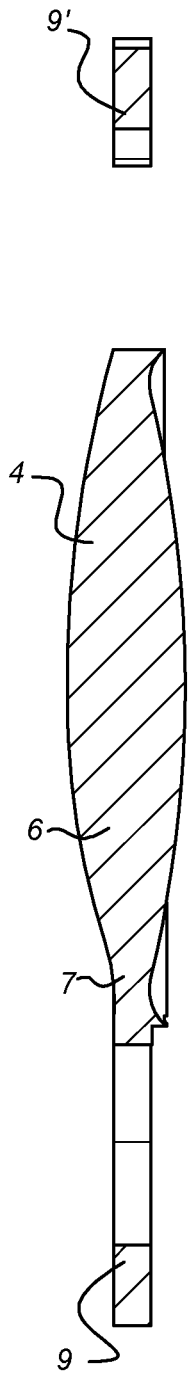
Figure 7:
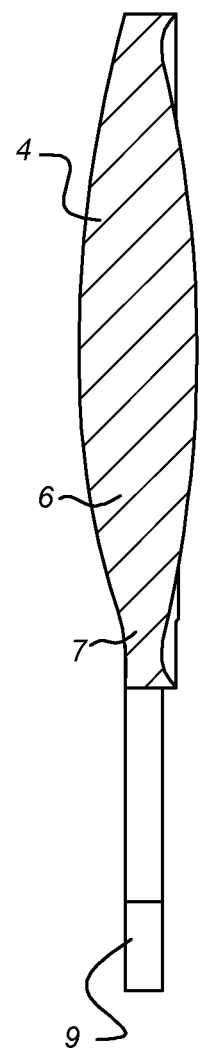
Figure 8:
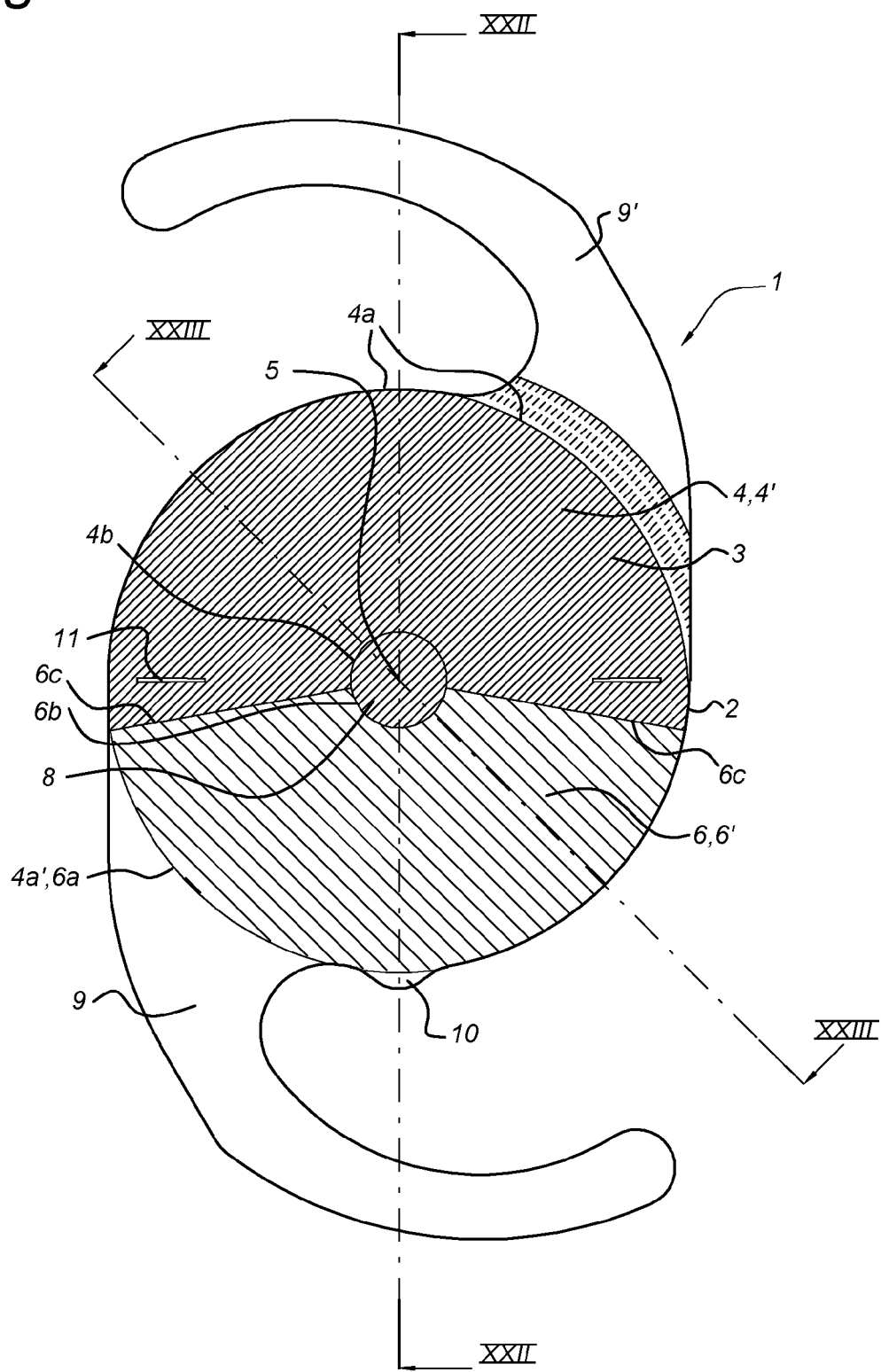
Figure 9:
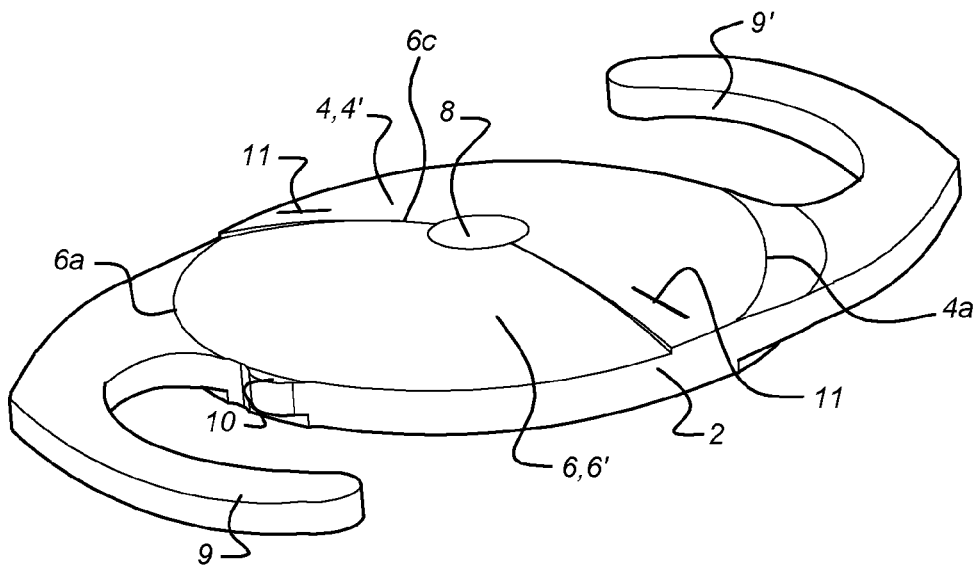
Figure 10:
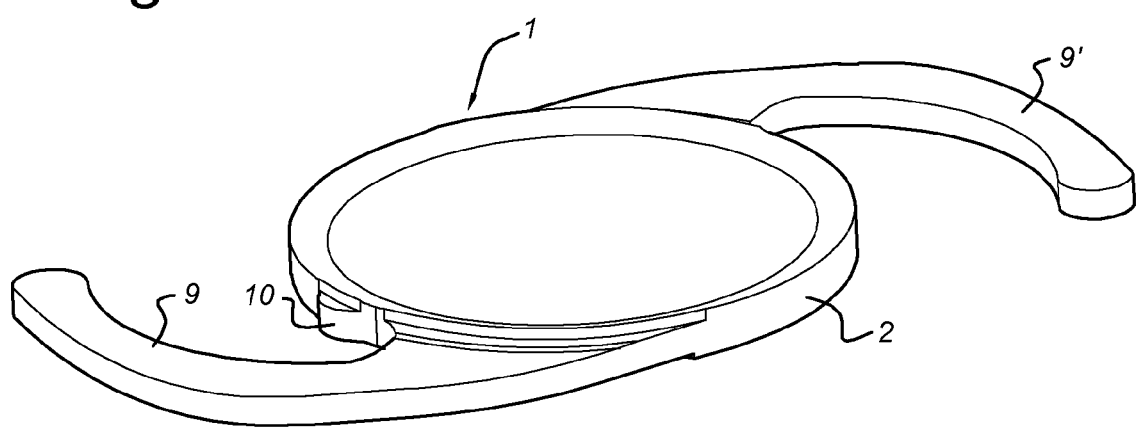
Figure 11:
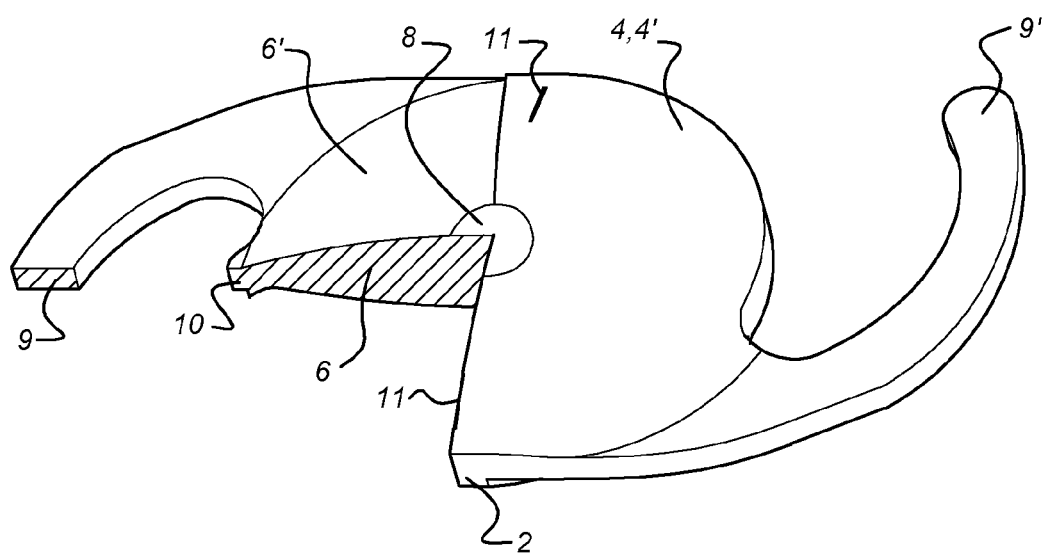
Figure 12:
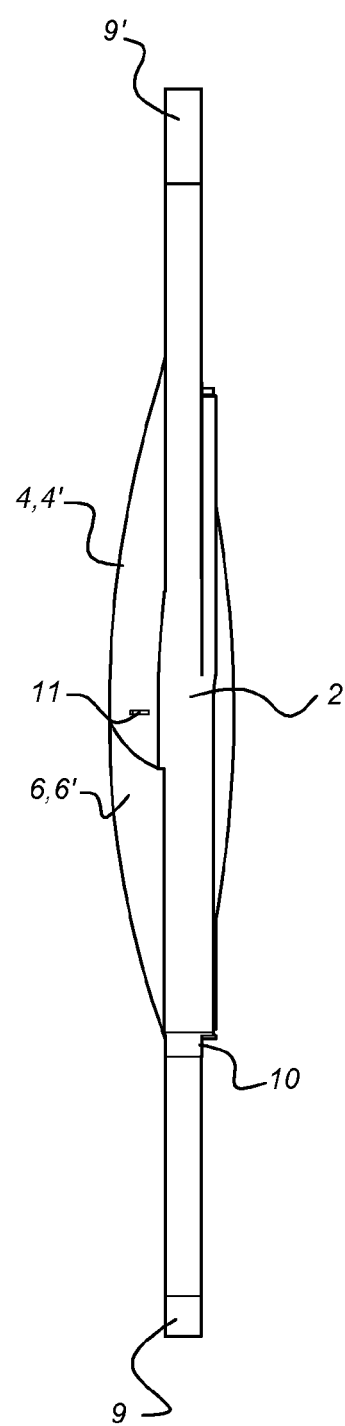

FIG. 1 a front view of an MSIOL with several regions of the lens hatched in different densities;

FIG. 2 a perspective view of the back of the MSIOL of FIG. 1;

FIG. 3 a perspective view of the front side of the MSIOL of FIG. 1 having a part taken away, thus showing the concave part;

FIG. 4 a perspective view of the MSIOL of FIG. 1, but without a central part;

FIG. 5 a side view of the MSIOL of FIG. 1;

FIGS. 6 and 7 the cross sections of the MSIOL of FIG. 1 as indicated in that figure;

FIGS. 8-14 several views of another embodiment of an MSIOL with raised or elevated lens, with respectively FIG. 8 a front view of an MSIOL with several regions of the lens hatched in different densities, with the recessed lens part elevated with respect to a plane of the haptics;

FIG. 9 a perspective view of the front side of the MSIOL of FIG. 8, also provided with a recessed part;

FIG. 10 a perspective view of the back of the MSIOL of FIG. 8;

FIG. 11 a perspective view of the MSIOL of FIG. 8, clearly showing that the lens is elevated, and having a part taken away;

FIG. 12 a side view of the MSIOL of FIG. 8, and

Figure 13:
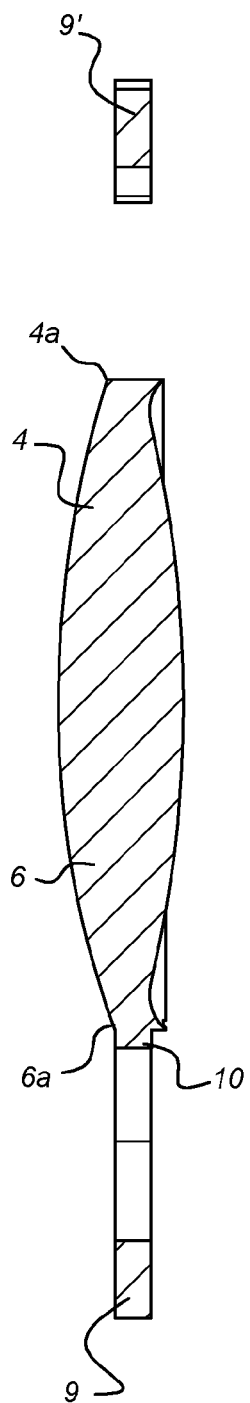
Figure 14:
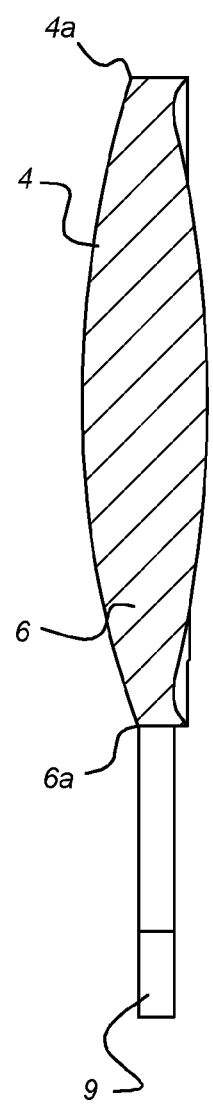
Figure 15:
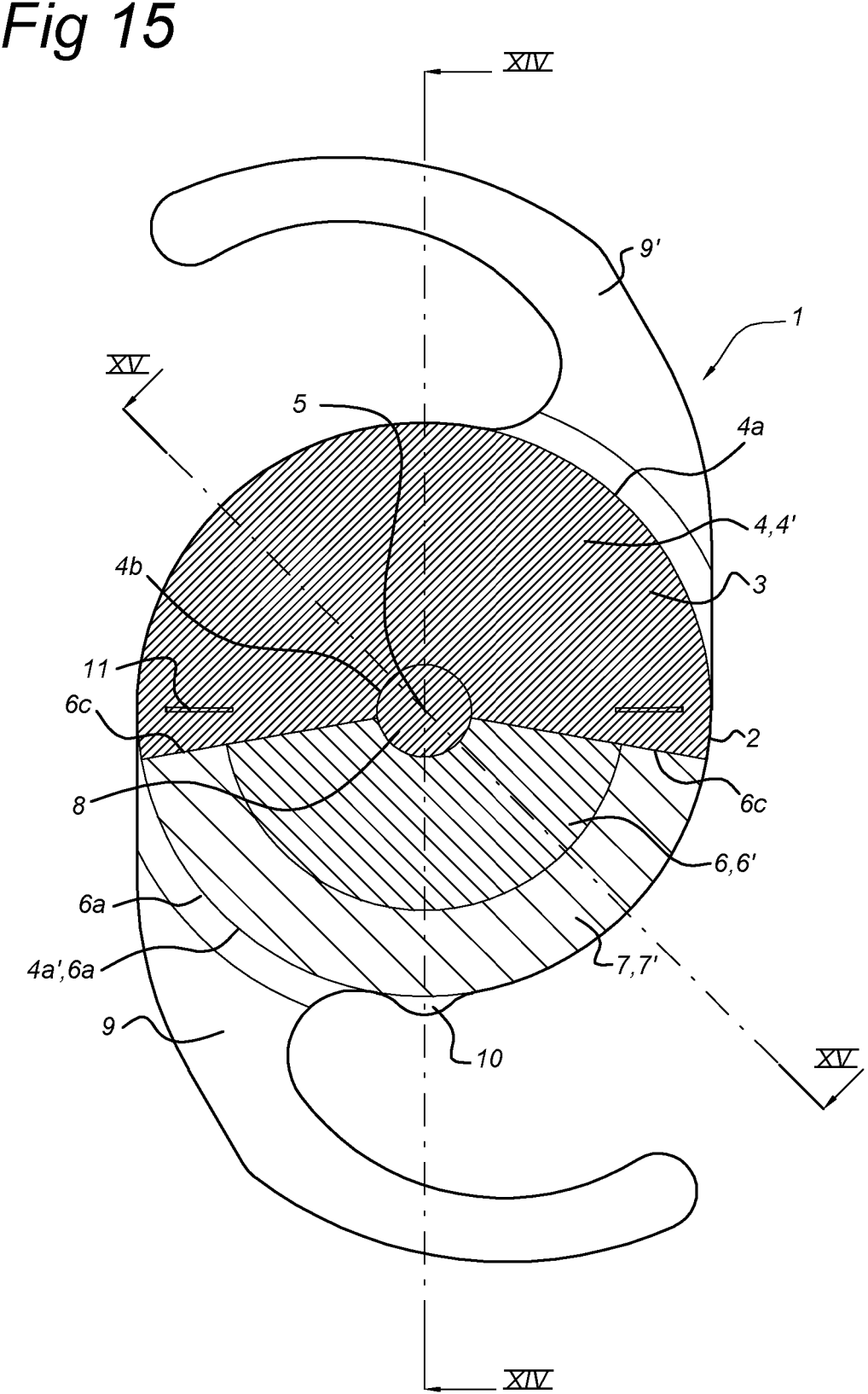
Figure 16:
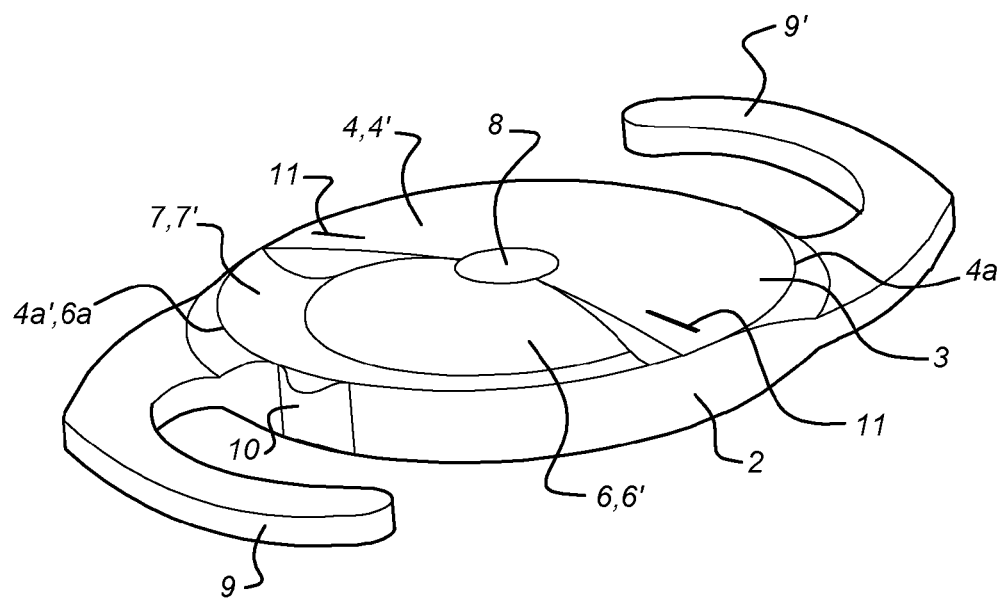
Figure 17:
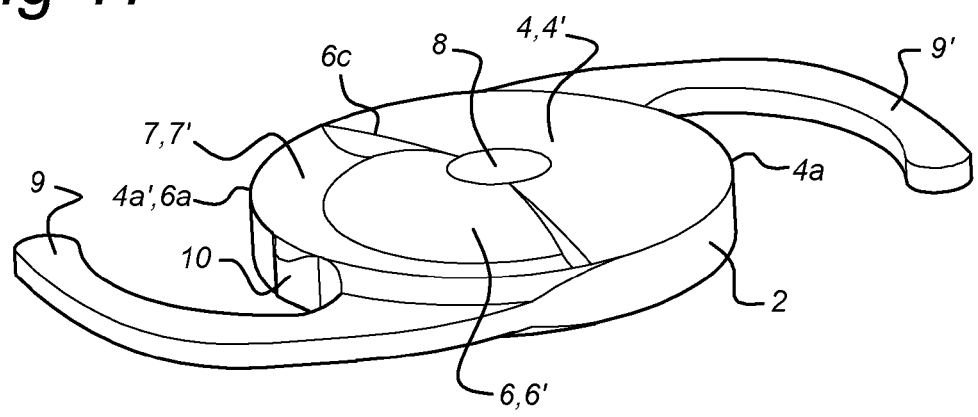
Figure 18:
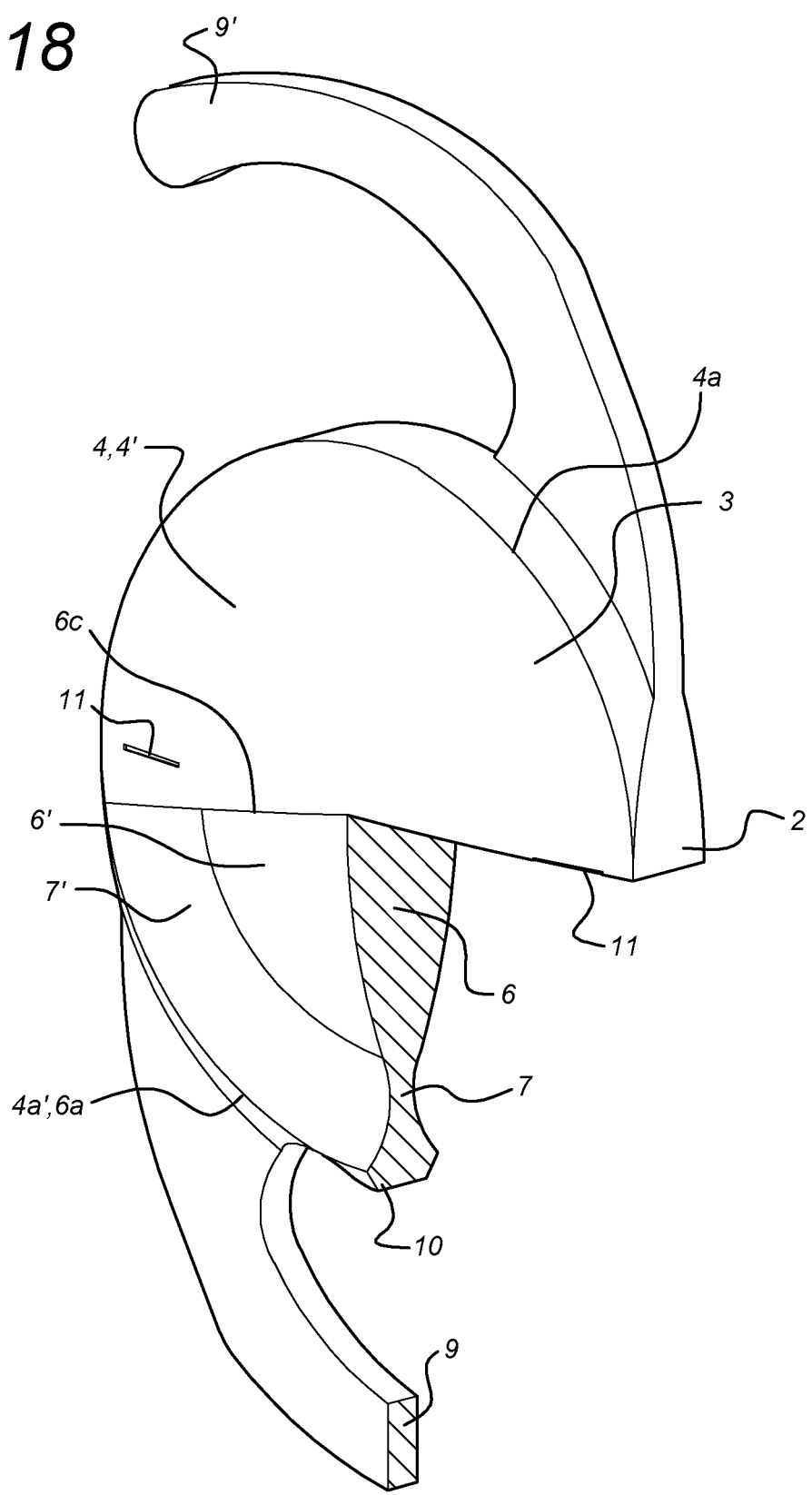
Figure 22:
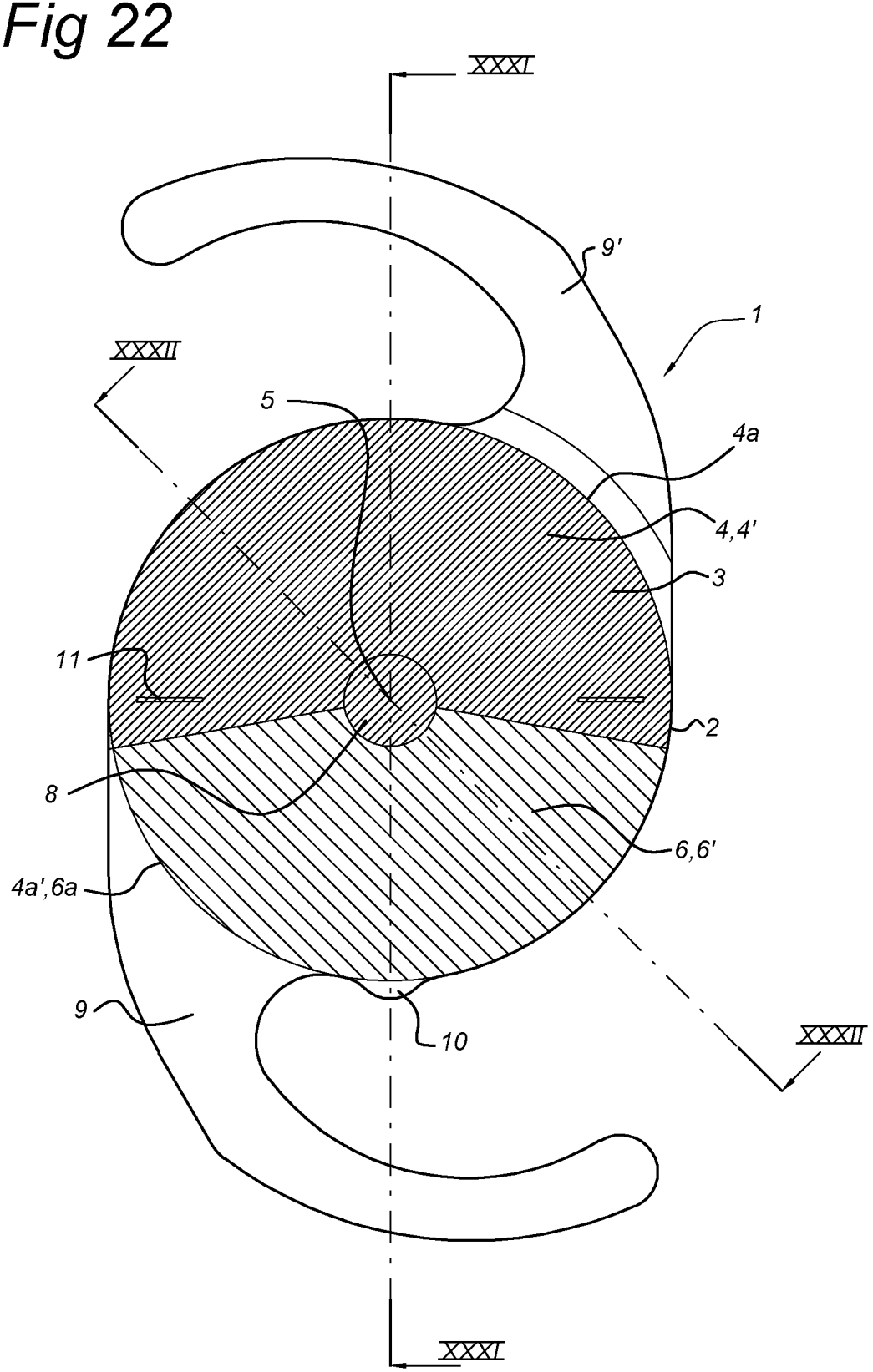
Figure 23:
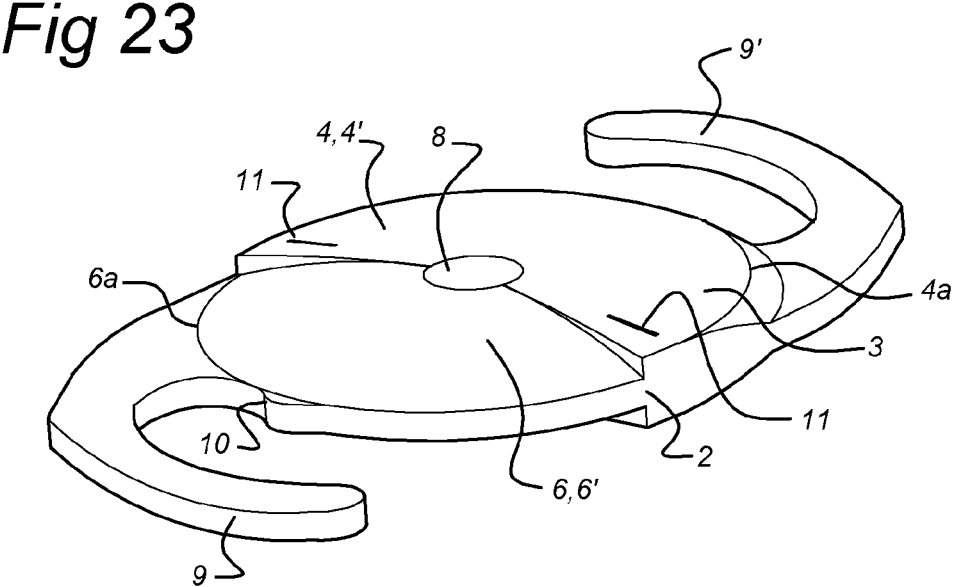
Figure 24:
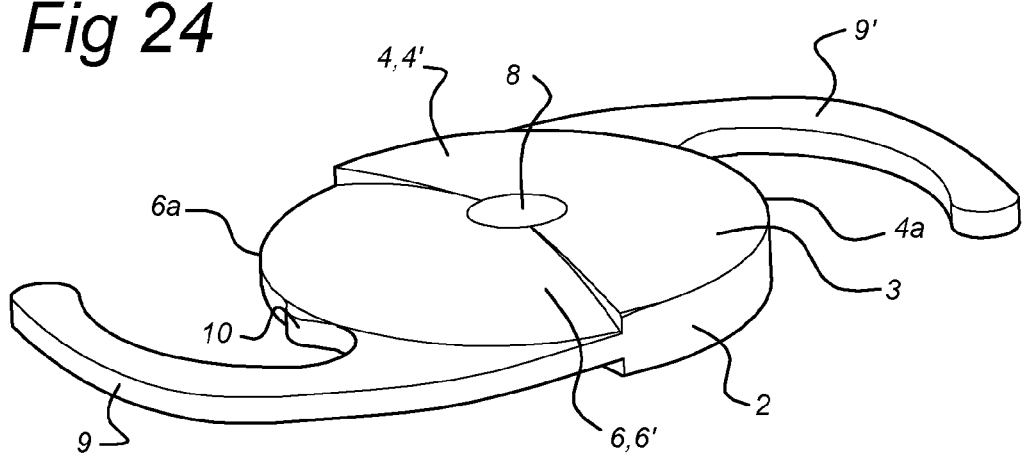
Figure 25:
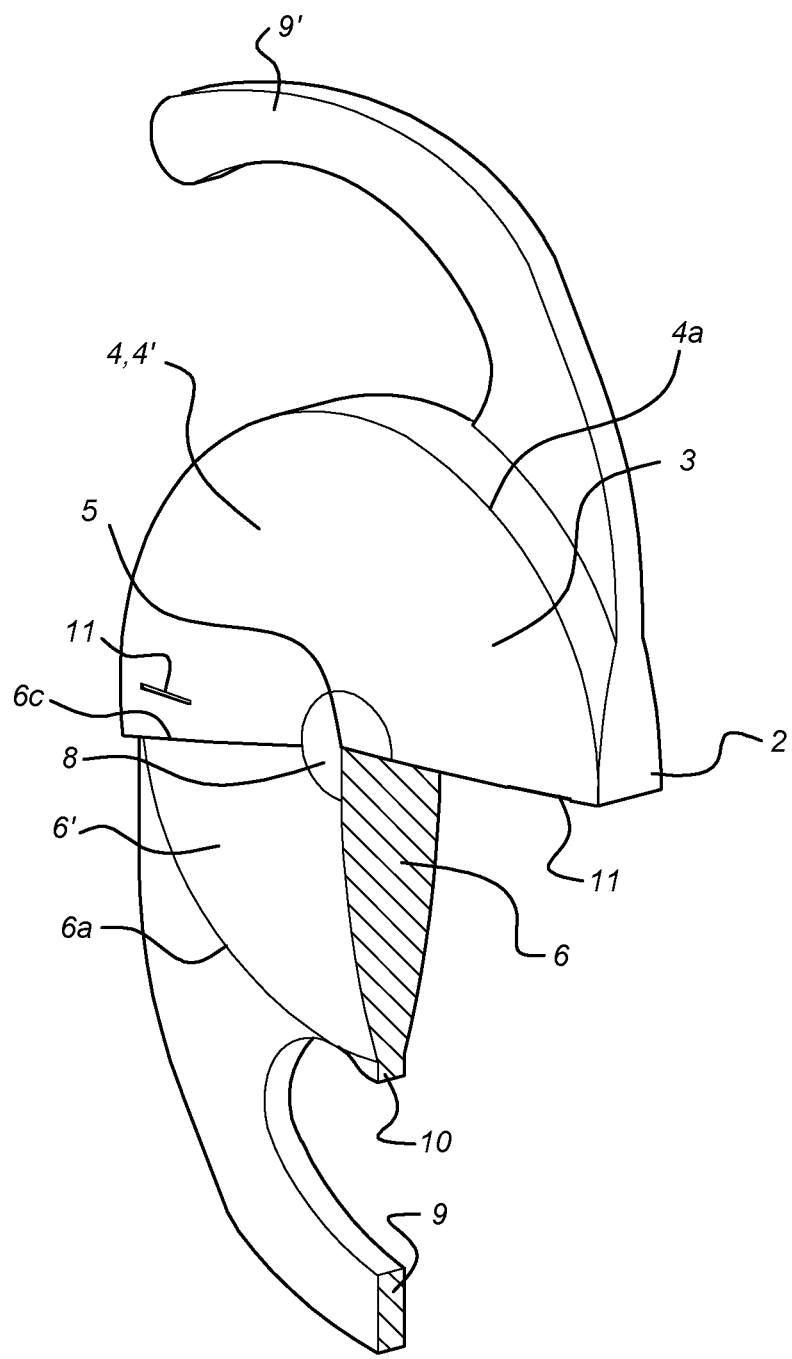
Figure 26:
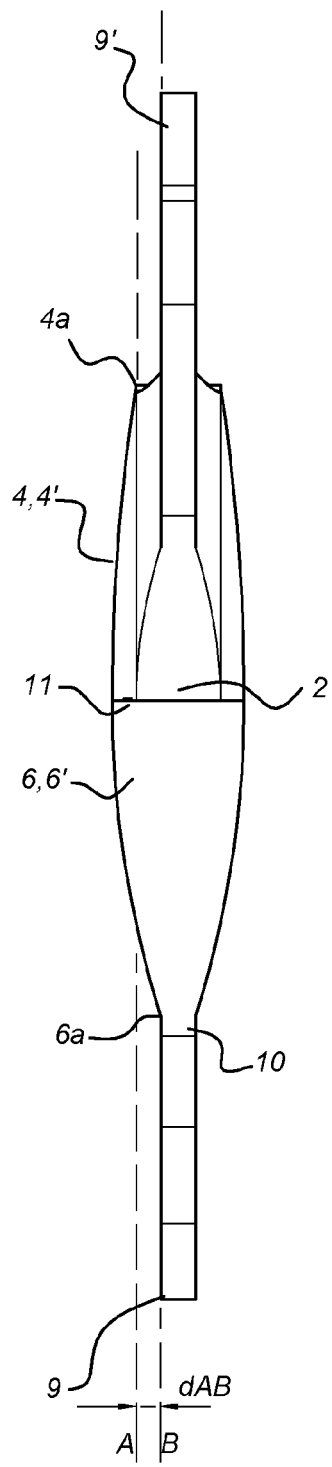
Figure 27:
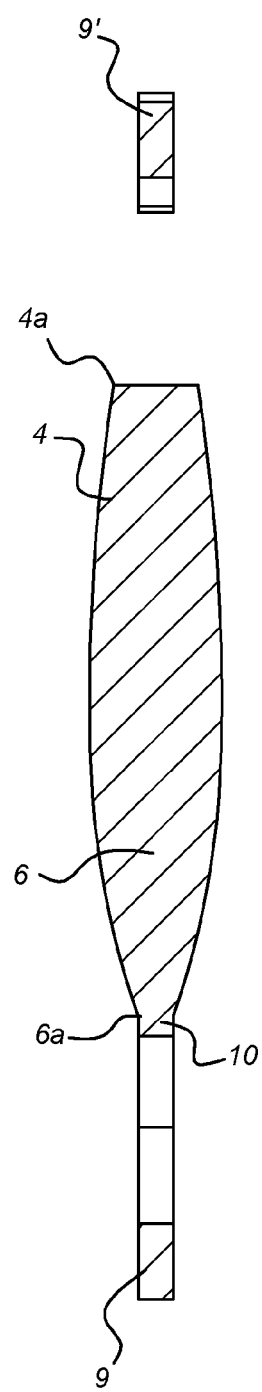
Figure 28:
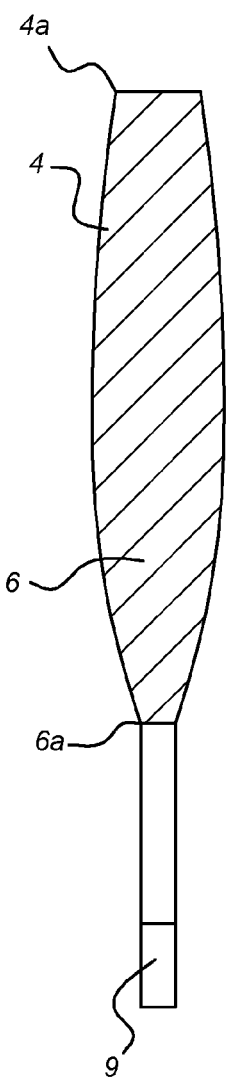
Figure 29:
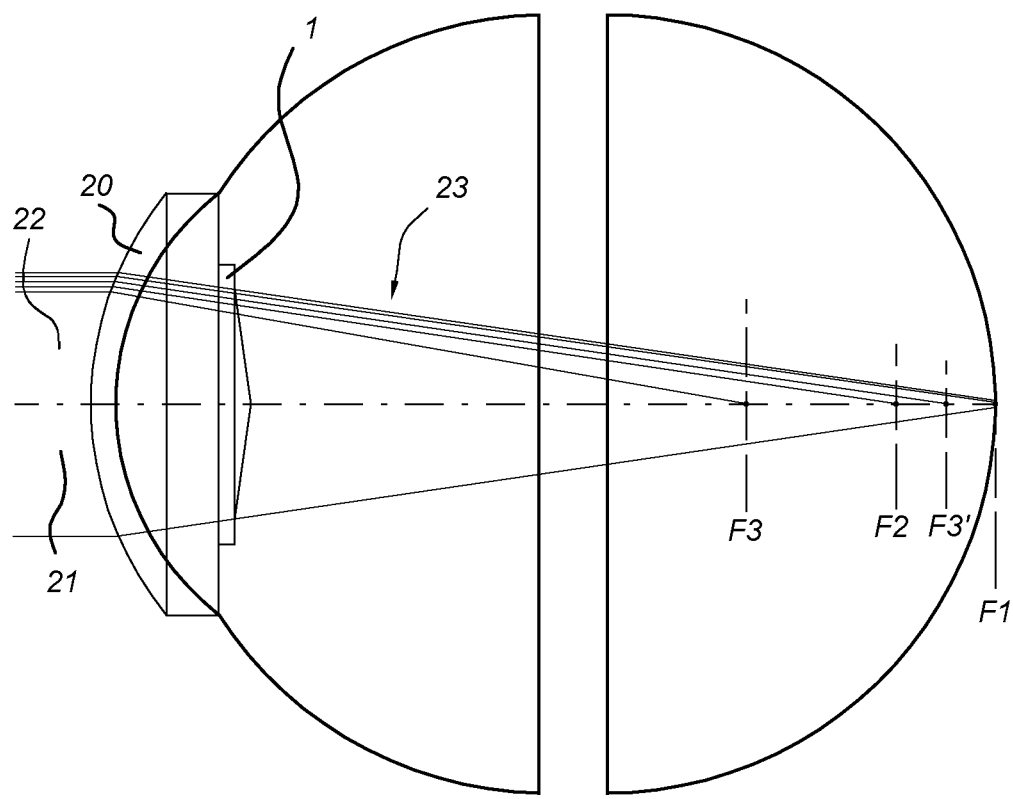
Figure 30A:
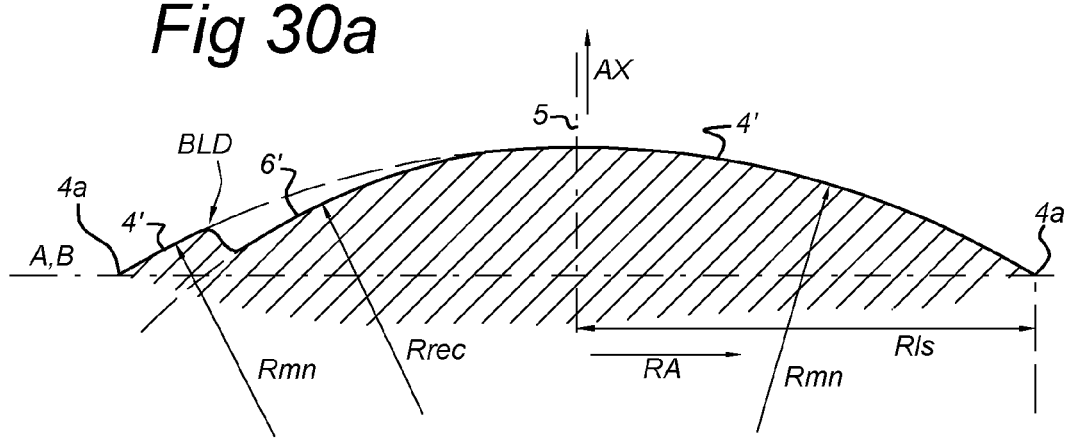
Figure 30B:
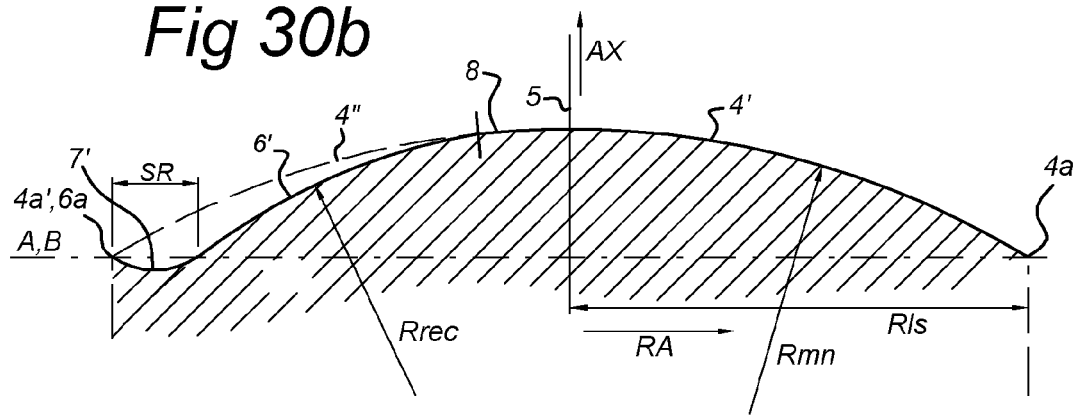
Figure 30C:
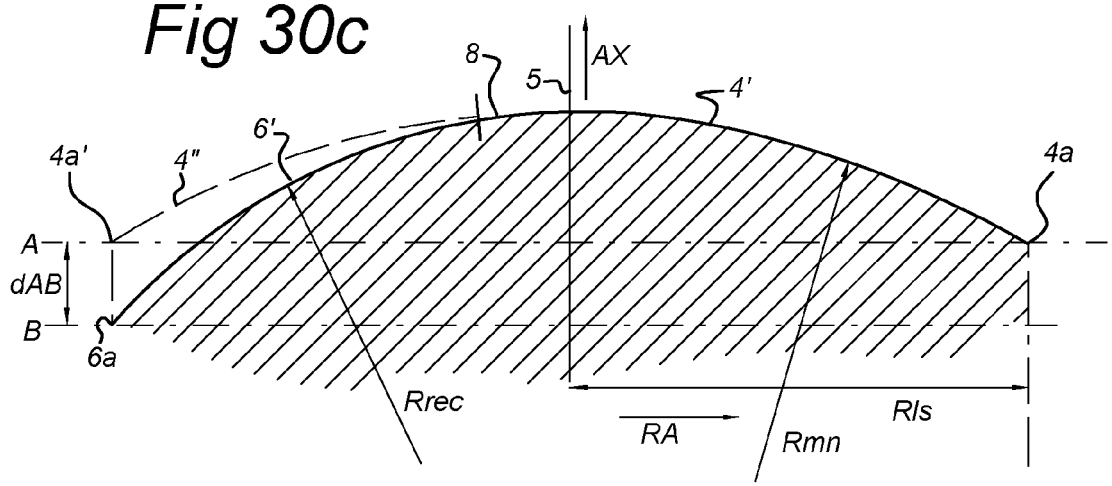
Figure 31:
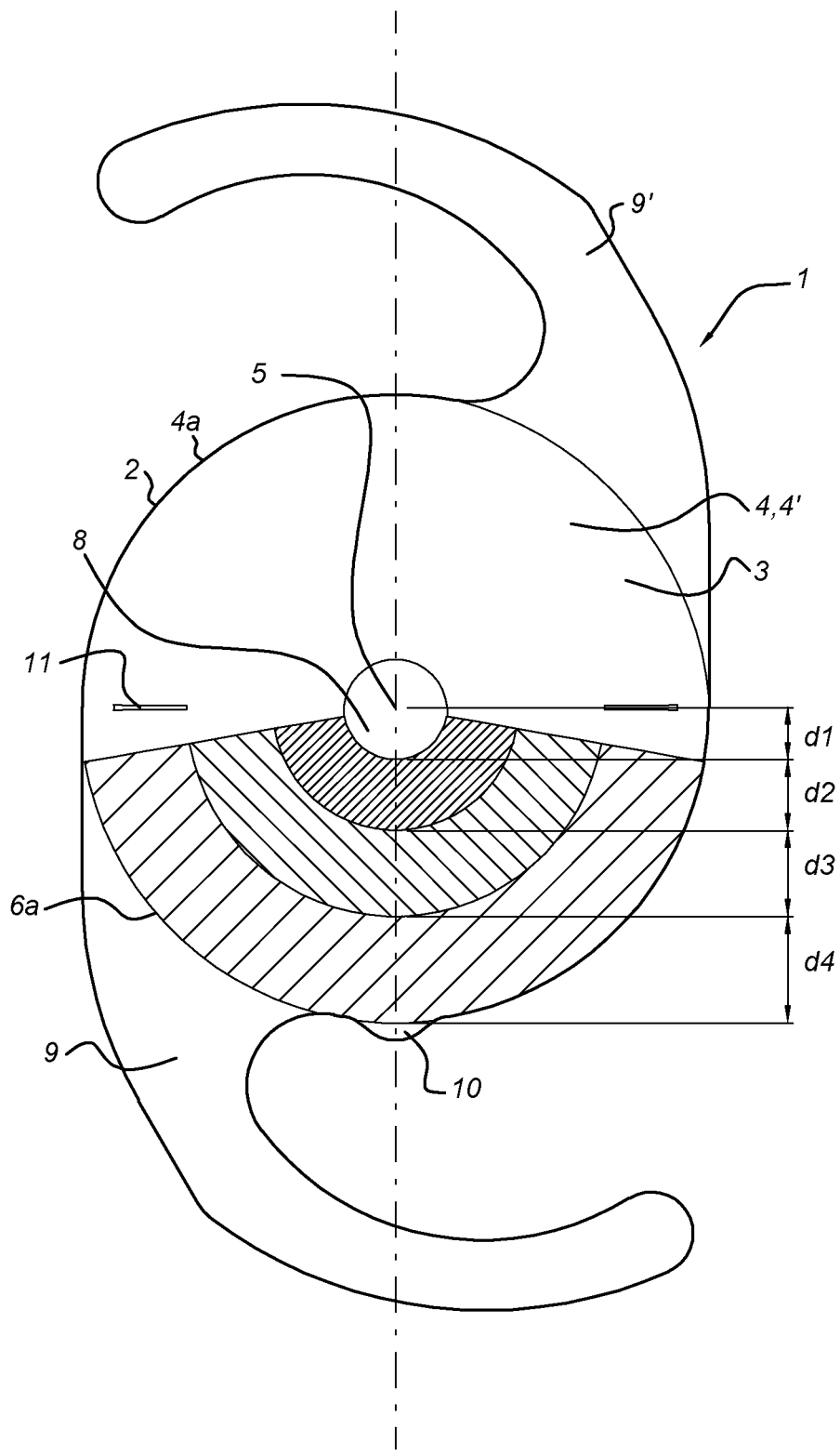

FIGS. 13 and 14 the cross sections of the MSIOL of FIG. 8 as indicated in that figure;

FIGS. 15-20 several views of another embodiment of an MSIOL with a concave region and a lens on both sides of the IOL, with FIG. 15 a front view of an MSIOL with several regions of the lens hatched in different densities, with the lens elevated with respect to a plane of the haptics;

FIG. 16 a perspective view of the back of the MSIOL of FIG. 15, also provided with a recessed part;

FIG. 17 a perspective view of the front side of the MSIOL of FIG. 15;

FIG. 18 a perspective view of the side of the MSIOL of FIG. 15 having a part taken away, thus showing the concave part on both sides;

FIG. 19 a side view of the MSIOL of FIG. 15;

FIGS. 20 and 21 the cross sections of the MSIOL of FIG. 8 as indicated in that figure;

FIGS. 22-28 several views of yet another embodiment of an MSIOL with raised or elevated lens and a lens on both sides of the IOL, with FIG. 22 a front view of an MSIOL with several regions of the lens hatched in different densities, with the lens elevated with respect to a plane of the haptics;

FIG. 23 a perspective view of the front side of the MSIOL of FIG. 22, also provided with a recessed part on the back;

FIG. 24 a perspective view of the back of the MSIOL of FIG. 22;

FIG. 25 a perspective view of the MSIOL of FIG. 22, clearly showing that the lens is elevated, and having a part taken away;

FIG. 26 a side view of the MSIOL of FIG. 22;

FIGS. 27 and 28 the cross sections of the MSIOL of FIG. 22 as indicated in that figure;

FIG. 29 an schematic ray path diagram of a state of the art MSIOL of applicant, showing the effect of an earlier circumferential or partial ring shaped blending part;

FIGS. 30a-30c respectively, a cross section of an IOL according to WO 2010/095938 A in FIG. 30a, an IOL of FIG. 1 in schematic cross section as indicated with line VI and showing only the front in FIG. 30b and an IOL of FIG. 8 in schematic cross section as indicated with line XXII and showing only the front in FIG. 30c, and FIG. 31 a front view of an IOL with several sectors.

DETAILED DESCRIPTION OF EMBODIMENTS

In the drawings, several embodiments of IOLs are discussed. In fact, as already explained above, these embodiments seek to avoid detrimental optical effects which result from the circumferential region of a recessed part remote from the optical axis of the lens region. This region of the lens can also be referred to as partial ring shaped region. In that respect, the lens region is the region of the intraocular lens (IOL) which is designed to project an image on the retina. In the drawings below, in fact four different designs are discussed. In all the designs, the lens region has a main lens region and a recessed lens region. This will be explained below. These designs provide different way in which the circumferential region of the recessed lens part matches the further IOL outside the lens region.

The IOL may be constructed of rigid biocompatible materials, such as polymehtylmethacrylate (PMMA), or flexible, deformable materials, such as silicones, deformable (meth) acrylic polymeric materials, hydro gels and the like which enable the optic to be rolled or folded for insertion through a small incision into the eye. Usually, the lens is made using a (turning) lathe or by moulding technology either partial or full mould.

With respect to the orientation and directions, the axial direction is defined to be along the optical axis, which is the optical axis of a main lens part, the radial direction is perpendicular to the optical axis and running from the optical axis in the direction of the circumference of the lens, and the tangential direction is perpendicular to the radial and axial directions.

In the first design, in an embodiment which is shown in FIGS. 1-7, the surface curvature of the circumferential region is adapted.

In the second design, shown in an embodiment in FIG. 8-14, the height of the lens region as a whole is increased, in other words, the lens or lens region is elevated, in such a way that at the lens circumference, the recessed part matches the further IOL surface or can be extra raised to such an extend that it still functionally be said to match the further IOL surface.

in an embodiment in FIGS. 15-20, showing a third design when higher relative dioptres of the recessed part are required, the rear surface of the IOL is used as an additional lens region. In this design, the circumferential or outer region of the recessed part again is concave. Furthermore, the lens regions on both the front surface and the back surface are elevated.

In the fourth design, shown in an embodiment in FIG. 22-28, again for relative higher dioptre recessed parts, the rear lens surface is again used as an additional lens, and this rear surface lens also has the increased height.

It should be clear that these four main designs all have further refinements further improving the IOLs. Furthermore, it should be clear that these designs can be combined.

FIG. 1 shows a front view of an IOL 1 which has a lens 3, the combined hatched or shaded parts. Lens 3 is in fact the ophthalmic lens. The lens 3 has an optical axis 5. The lens has a circumference 2, which usually is circular or almost circular. In some designs, for instance for so called toric lenses, the circumference 3 can be elliptic. It is most clearly visible in the side view and cross sections of FIGS. 5-7 that the front surface of the haptics 9 and 9' is in one plane together with circumference 2 at the front surface side (anterior side for facing away from the posterior chamber of the human eye). In this way, the thickness of the IOL near the circumference 2 is ensured. Many of the details of the current IOL 1 are disclosed in WO 2010/095938 A, which is incorporated by reference as if fully set forth. In fact, many of the dimensions and shapes are described in this publication.

In the design of FIG. 1, the lens 3 has a main lens region 4 that is indicated with the densest hatches. The main lens region 4 is usually (commonly) used in far vision (distance vision). In most common designs, this main lens part (or its main lens surface 4') has an optical power of between −20 dioptre and about +35 dioptre. When circular, the main lens region 4 has a diameter d which usually is about 5-7 mm. The main lens part 4 extends in an outward radial direction to a main lens outer circumference 4a remote from the main optical axis 5.

The lens 3 further has a recessed part. This recessed part is indicated with the other two hatched parts 6 and 7. In fact, the recessed part 6, 7 has a recess surface 6', 7' which is below an imaginary extension 4" (shown in FIGS. 30a, 30, and 30c) of the surface 4' of the main lens region 4. In this design the recessed part 6, 7 has a near part 6 (having recess surface 6') that is indicated with the second densest hatching. This near part 6 (or its recess surface 6') usually has a relative positive dioptre with respect to the main lens region 4 (or its main lens surface 4', respectively), and is usually used in near vision such as in reading. In case both the main lens surface 4' and the recess surface 6' are purely spherical or aspherical lens surfaces, the main lens surface 4' has a radius of curvature which is larger than the radius of curvature of recess surface 6. The near part 6 usually has an optical power of about +1.0 to about +5.0 with respect to the optical power of said main lens part 4. Thus, the lens region 3 in fact incorporates two optics, namely main lens part 4 and near lens part 6. They are disposed in such a way that their optical axes coincide. Thus, in this design the optical axis of near part 6 coincides with main optical axis 5 of the main lens part 4. More in general, to result in an optically acceptable design the optical axes of the main lens part and the recessed part should be within an Airy Disc circle of about 0.1 mm. The near part 6 of recessed part 6 extends a radius dR from the optical axis 5 of about 1.5-2.8 mm. It should be clear that the actual dimensions of the lens region and of the lens parts can also depend on the actual pupil size of a person wearing the IOL. Thus, the larger values are often used for a person that has a large pupil diameter.

The recessed part further has a circumferential region 7 that is indicated with the least dense hatches. This circumferential region 7 in fact matches the part of near part 6 that is remote from the optical axis 5 with the rest of the IOL 1. Thus, it can also be referred to as circumferential blending part 7 of partial ring blending part 7. It in fact can be considered as a blending part matching the near part 6 to the circumference 3 of the lens 2. It can also be referred to as the concentric peripheral blending part 7. The recessed part usually includes an angle of between 120 and 200 degrees. Thus, the circumferential region 7 extends between 120 and 200 degrees.

In FIG. 3, in the part taken away along two radial directions, the profile in radial direction of the circumferential region is illustrated. In an earlier designs of an IOL, which is for instance disclosed in WO 2010/095938 A, this circumferential region 7 in fact had for its largest part a curvature which was the same as the curvature of the main lens part 4. The surface of the near part 6 would continuously but steeply rise up to the level of the surface 4' of the main lens part 4 at that axial position, as shown in FIG. 30a. The lens part 7 from that axial position would then continue axially the same as the main lens part 4. The meridian or substantially radial blending zones 6c which match main lens part 4 and the recessed part 6, 7, or blend the main lens part 4 and the recessed part 6, 7, can be shaped as described in WO 2010/095938 A.

In the current design, in contrast, the outer boundary of the near part 6 is matched to the circumference of the lens 3 in a different way. The near part 6 is continued in axial direction until it is at least at the level of the circumference of lens 3. This means that the recessed part extends in the outward radial direction to an outer boundary of the recessed part remote from the main optical axis 5 and that this outer recess boundary extends along or beyond the outer circumference of the lens 3 as seen in an outward radial direction. The outer circumference of lens 3 in the region of the recessed part may be imaginary. Such outer imaginary circumference section 4a' is better defined with respect to the main lens 4 and can be regarded as an imaginary outer circumference section 4a' that would have at least partially provided a main lens outer circumference together with an actual outer circumference section 4a of the main lens 4 in case the recessed part would have been absent. The outer recess boundary 6a can be at a distance from main optical axis 5 which is equal to or larger than a distance of the imaginary main lens outer circumference section 4a' from main optical axis 5 in a same radial direction.

The recessed part 6, 7 has a recess surface that is recessed with respect to an imaginary main lens surface section 4", which would have been part of the main lens surface 4' in case the recessed part would have been absent. The imaginary main lens surface section 4" is indicated in FIGS. 30a, 30b and 30c. Both the main lens outer circumference section 4a and the main leans surface 4' define the imaginary main lens outer circumference 4a' and the imaginary main lens surface section 4".

The imaginary main lens outer circumference section 4a' and the imaginary main lens surface 4" may essentially be defined by mirror symmetry with respect to a mirror plane comprising the main optical axis 5. Such mirror plane can, for instance, pass through the main optical axis 5 and both markings 11 that are visible in FIGS. 1, 3 and 4, and also in other figures, but mirror planes defined in another fashion may also apply. The imaginary main lens outer circumference section 4a' and the imaginary main lens surface 4" on one side of such mirror plane essentially coincide with mirror images of part of the main lens outer circumference section 4a and part of the main lens surface 4', respectively, on the other side of the mirror plane.

In another or a same embodiment, the imaginary main lens outer circumference section 4a' and the imaginary main lens surface 4" may essentially be defined by line symmetry with respect to main optical axis 5. The imaginary main lens outer circumference section 4a' and the imaginary main lens surface 4" on one side of main optical axis 5 essentially coincide with mirror images of part of said the lens outer circumference section 4a and part of the main lens surface 4', respectively, on the other side of the main optical axis.

In the various embodiments shown in the figures both definitions for the imaginary main lens outer circumference section 4a' and the imaginary main lens surface 4" apply. However, in other embodiments that can me envisioned, one of both definitions can apply, or the imaginary circumference section and imaginary main lens surface may be envisioned in another way. Such an embodiment could be one having a lens 3 with an elliptic circumference that would be a circumference of the main lens 4 in absence of a recessed part, and having a recessed part positioned about symmetrically on both sides of a symmetry axis of the elliptical circumference.

The recess surface can have a transition part that in axial direction continuously matches the curvature of the near part 6 but changes in axial direction from going downward into going upward, to circumference 6a and resulting in the concave circumferential region 7, as shown, inter alia, in FIG. 30b. This provides a region shaped such that it diverges light rays. In that way, light on that region will not be projected on a visual image on the fovea. In other words, for a person wearing the IOL it will not result in a visual feature or artefact in light conditions when the pupil is so large that light impinges upon the circumferential region 7 and is projected upon the fovea.

The IOL 1 further has haptics 9, 9' which are known in the art in will not be discussed further. A known alternative for the haptics 9, 9' are so called plate haptics. The front surface of these haptics usually coincide with the circumference of the lens 3 at that same side.

On the main lens region 4, two markings 11 are made which can be used by an eye surgeon in order to position the IOL 1. This IOL 1 further has an indication 10 which can also be used by an eye surgeon in order to find the lower part of the IOL 1.

The main lens 4 further has a central part 8 that has already been extensively discussed in WO 2010/095938 A. When light levels are such that the pupil has about the diameter of a circle enclosing of bounding the central part 8, the depth of focus will be such that most people do not need a near part 6 for instance for reading. This central part 8 usually is bounded by a circle that has a diameter of about 0.2-3 mm. More in particular, its diameter is about 0.2-2 mm. In most cases, a diameter of about 0.2-1.6 is sufficient. At its circumference, which is an inner circumference 4b of the main lens part 4 and an inner circumference 6b of the recessed part, the surface of central part 8 radially smoothly changes curvature to match the curvature of the main lens surface 4' or the recess surface 6', respectively. In FIG. 4, an example is given of an IOL without this central part 8.

An example of the back or rear side (or posterior side for facing towards the posterior chamber of the human eye) of the IOL 1 is shown in FIG. 2. In this embodiment, the design of the side is known from for instance WO 2010/095938 A, or it can have the design as described in PCT/NL 2009/050341. The features of the back of this embodiment will not be discussed further.

As mentioned above, in the second design, shown in an embodiment in FIG. 8-14, the height of the lens region as a whole is increased, in other words, the lens or lens region is elevated, in such a way that at the lens circumference, the recessed part matches the further IOL surface. What this may look like is shown in FIGS. 8-14. Large part of the outer circumference 4a of the main lens part 4 is thus raised with respect to the outer circumference 6a of the recessed part 6. The circumference of the lens 3 is in this way no longer in one plane.

In an alternative embodiment of FIG. 8, the main lens part 4 at the position of haptic 9' continues on the haptic 9', beyond the boundary 4a of a circle which normally is the circumference 2. Such continuation (shown on dashed line hatching) is just for practical purposes and may or may not be a continuation of the main lens surface or just a blending region. In such alternative embodiment the imaginary main lens outer circumference section 4a' and the imaginary main lens surface 4" are defined by both mirror symmetry of a section of main lens outer boundary 4a and main lens surface to the left of line XXII-XXII in FIG. 8 in a mirror plane containing main optical axis 5 and both markings 11, and line symmetry of the same section of main lens outer boundary 4a and main lens surface to the left of line XXII-XXII with respect to main optical axis 5.

Another design of that part of the main lens part 4 is illustrated in FIG. 9. There, beyond the circular circumference 4a at haptic 9', the slope of the main lens 4 is increased rapidly to match the surface of haptic 9'. In an extreme design, the main lens 4 can be ended at haptic 9' in a step to match the surface of haptic 9'. It is evident that the rapid slope part is not part of the lens. In the example of FIG. 9, circumference 2 is circular.

The design of such an IOL 1 usually takes the following steps. First, the required dioptre of the main lens part 4 and the recessed part 6 are determined. Thus, the radius of curvature of surfaces of both parts is determined. Next, the diameter of the central part 8 is determined. Subsequently, the required lens diameter is determined. Next, the lens height in axial direction will be determined in such a way that the outer recess boundary 6a of the steepest part of the recessed part 6 crosses a first lens plane at the required diameter. As the main lens part 4 has a larger radius of curvature than the recessed part, it means that at the required diameter, outer circumference section 4a of the main lens 4 will be in a second lens plane remote from the first plane.

The design shown in FIGS. 15-21 relates to an IOL which has the circumferential region of the design of FIGS. 1-7. In this particular design, additionally, the back of the IOL is also provided with a lens region. In particular in FIG. 17, the reverse side or back of the IOL of FIGS. 15 and 16 is shown. In this particular design, the lens region on the back of the IOL is a mirror copy of the lens on the front side. In this way, the dioptre and other optical properties of the lenses can in fact be divided over two lens surfaces. In particular for higher required dioptres, it is possible to keep the dimensions of the lens within the design possibilities. Furthermore, when dividing the optical properties, the various blending parts which are needed for blending the main lens part 4 and the recessed parts can be less steep, or alternatively their width can be reduced. In fact, in such a design the sum of the recessed part on the front and on the back of the lens can have a relative dioptre with respect to the sum of both main lens parts of about +6.0 or more.

In the design of FIGS. 22-28, the designs of FIGS. 8-14 and of FIGS. 15-21 are combined. In fact, in this embodiment there is a lens region on the front and the back of the IOL. Furthermore, each of the lens regions has a main lens part 4 and a recessed part 6 that has the same design as in FIGS. 8-14. In particular when higher dioptres of the various lens parts are required, or larges differences between parts of the lens region are required, this has advantages. FIG. 26 shows that main lens outer circumference section 4a and therefore imaginary main lens outer circumference section 4a' is in a first plane A, and that outer recess boundary 6a is in a second plane B. First plane A is located at a distance dAB from second plane B in an axial direction outward of the lens.

In FIG. 29, the problem which arises with the design of the circumferential region which was shown in WO 2010/095938 A is illustrated. The design is for instance shown in FIG. 7 of that publication. In that design, the main lens continues at the radial end of the recessed part. Thus, a blending zone is requires in such a design.

In the schematic drawing of FIG. 29, and IOL has a main lens part with focus F1 and a recessed near part with focus F2. It was found that the blending zone as well as the additional main lens part results in several additional foci, indicated with F3 and F3'. These additional foci can result in additional, unwanted light spots on the fovea: In the schematic drawing, the light rays stop at their respective foci F3 and F3'. In real live, however, these rays result in one or more blurred spots at positions on the fovea next to a real image.

The IOL of the current invention can be produced using machining, in a way already described in WO 2010/095938 A. This part should therefore be considered to be cited by reference as if incorporated in this description.

Two embodiments of the invention are further explained in FIGS. 30b and 30c in comparison with the prior art IOL of WO 2010/095938 A in FIG. 30a. In these drawings, the lens plan is indicated with ZL PL (Z-level Plane). Rmn is the radius of curvature of the main lens region, Rrec is the radius of curvature of the recessed part. Furthermore, radial direction RA and axial direction AX are indicated. Rls is the radius of the lens. In FIGS. 30a-30c, the recessed part 6 has a radius of curvature that is smaller than the radius of curvature of the main lens region 4. The small line part close to reference number 8, indicating the central part, is the end of the central part. When starting from optical axis 5, up to that position the surface has the radius of curvature Rmn. In the state of the art design of FIG. 30a, the recessed part 6 continuously fits a blending zone BLD and continuous fits an outer part that has the radius of curvature of the main lens part, the outer part. The stripes line indicates the continuation of the main lens surface 4' and represents imaginary main lens surface 4". It was found that when a pupil is very large, some light from parallel incoming light on the cornea and passing the pupil can impinge on this outer part. This light will be projected in the focal plane of the main lens part, but a little offset with respect to the optical axis. This results in blur or artefacts.

In FIG. 30b, the recess surface 6' of recessed part in radial direction ends at about plane B. After that radial position, the surface continuous in a continuous, smooth way to get back to plane B, which contains outer recess boundary 6a. Thus, a part indicated SR will be concave. When the some light from the collimated beam impinges on that IOL part, it will diverge away from the optical axis 5. Main lens outer circumference section 4a is within a plane A, planes A and B coinciding in FIG. 30b. Imaginary main lens outer circumference 4a' and outer recess boundary 6a (essentially) coincide in FIG. 30b. FIG. 20 also shows planes A and B coinciding for the embodiment shown in FIGS. 15-21. Furthermore, the embodiment of FIGS. 15-21 has planes A and B on the anterior side of the IOL and planes A and B on the posterior side of the lens.

In the embodiment of FIG. 30c the main lens part is raised in axial direction to such an extent that the recessed part ends at plane B radially at the steepest part of recess surface 6' having the smallest Rrec. In this case, the circumference of the main lens part is essentially in plane A that is axially a distance dAB away from, or above, plane B. In some specific embodiments, for instance like in FIGS. 8 and 11, part of the main lens is continued for instance on a haptic 9'. In another specific embodiment, shown in FIG. 9, at the circumference a transition zone is created. At this transition zone, the height rapidly decrease to plane B when going in radial direction.

In FIG. 31 a front view of an IOL with a recessed part with several sectors is shown. The IOL has a lens 3 with circumference 2. The IOL has a main lens part 4 with a central part 8. The central part usually has a width d1 of about 0.1-0.6 mm as explained above. In this embodiment, the recessed part is hatched and has several sectors, each having a different type of shade. Closest to the central part is a first sector. This sector usually has a dioptre which is between +1.0-+5.0 dioptre with respect to the optical power of the main lens part 4. This sector extend a width d2 of 0.1-1.0 mm from the central part in radial direction. The surfaces of the central part and the first sector match, but the surfaces do not need to match continuously. The surface of the second sector matches the first sector. It has a dioptre of about +1.00-+5.00 Dioptre with respect to the main lens part 4. It has a width d3 of 0.2 to 1.6 mm. The recessed part has a third sector that extends a width d4 of 0.2-1.50 mm. It has a relative dioptre of between −1.00-+1.00 dioptre with respect to the main lens part 4. In one design, the different values were selected:

Lens diameter=6 mm

|    | Example 1 | | Example 2 | | Example 3 | |
|----|-----------|--------|-----------|--------|-----------|--------|
|    | Width | Dioptre | Width | Dioptre | Width | Dioptre |
| d1 | 0.35 |  | 0.15 |  | 0.50 |  |
| d2 | 0.25 | +1.00-+2.25 | 0.50 | +2.25 | 0.30 | +3.50-+2.50 |
| d3 | 1.20 | +3.0 | 1.20 | +3.5 | 1.00 | +2.25 |
| d4 | 1.20 | Main-+0.50 | 1.15 | −1.0-main | 1.20 | main |

|    | Example 4 | | Example 5 | |
|----|-----------|--------|-----------|--------|
|    | Width | Dioptre | Width | Dioptre |
| d1 | 0.30 |  | 0.30 |  |
| d2 | 0.80 | +3.50 | 0.70 | +3.0 |
| d3 | 0.90 | +1.75 | 1.20 | +2.25 |
| d4 | 1.00 | main | 0.80 | Main-+1.00 |

In another example of an IOL, the IOL has a lens 3 with circumference 2. The IOL has a main lens part 4 with a central part 8. The central part usually has a width d1 of about 0.1-0.6 mm as explained above. In this embodiment, the recessed part has two sectors. Closest to the central part is a first sector. This sector usually has a dioptre which is between +1.0-+5.0 dioptre with respect to the optical power of the main lens part 4. This sector extend a width d2 of 0.1-2.4 mm from the central part in radial direction. The surfaces of the central part and the first sector match, but the surfaces do not need to match continuously. It has a relative dioptre of between −1.00-+1.00 dioptre with respect to the main lens part 4. In one design, the different values were selected:

Lens diameter=6 mm

|    | Example 6 | | Example 7 | | Example 8 | | Example 9 | |
|----|-----------|--------|-----------|--------|-----------|--------|-----------|--------|
|    | Width | Dioptre | Width | Dioptre | Width | Dioptre | Width | Dioptre |
| d1 | 0.30 |  | 0.15 |  | 0.55 |  | 0.20 |  |
| d2 | 1.50 | +1.5-+3.0 | 1.70 | +1.5-+3.5 | 1.30 | +1.5-+3.5 | 1.60 | +1.5-+3.5 |
| d3 | 1.20 | main | 1.15 | main | 1.15 | main | 1.20 | main |

In the designs presented, one of the objectives is to avoid optical problems of the end of the recessed part. Another objective is to provide the recessed part in such a way that the thickness of the IOL at the recessed part remains at least 0.20 mm.

It will also be clear that the above description and drawings are included to illustrate some embodiments of the invention, and not to limit the scope of protection. Starting from this disclosure, many more embodiments will be evident to a skilled person which are within the scope of protection and the essence of this invention and which are obvious combinations of prior art techniques and the disclosure of this patent.

The invention claimed is:

1. An intraocular lens having a lens comprising:
    the lens comprising a main lens part having a main lens surface and a main optical axis defining radial, tangential and axial directions, the main lens part being configured for optimizing distance vision of a person provided with the intraocular lens; and
    a recessed part having a recess surface and extending between said main optical axis and a circumference of said lens, said recessed part comprising a secondary lens part with a secondary lens surface having a positive relative optical power with respect to an optical power of said main lens surface, the secondary lens part being configured for optimizing near vision and/or intermediate vision of the person provided with the intraocular lens,
    said main lens surface extending in an outward radial direction towards a main lens outer circumference section remote from said main optical axis, said main lens outer circumference section coinciding with said circumference of said lens,
    said main lens outer circumference section and said main lens surface defining:
        an imaginary main lens outer circumference section that would have at least partially provided a main lens outer circumference together with said main lens outer circumference section in case said recessed part would have been absent; and
        an imaginary main lens surface section that would have been part of said main lens surface in case said recessed part would have been absent, said recess surface being recessed with respect to said imaginary main lens surface section, said main lens outer circumference section and said main lens surface further define an imaginary main lens outer circumference section that would have at least partially provided a main lens outer circumference together with said main lens outer circumference section in case said recessed part would have been absent, said imaginary main lens outer circumference section and said imaginary main lens surface essentially being defined by mirror symmetry with respect to a mirror plane comprising said main optical axis, said imaginary main lens outer circumference section and said imaginary main lens surface on one side of said mirror plane essentially coinciding with mirror images of part of said main lens outer circumference section and part of said main lens surface, respectively, on the other side of said mirror plane, wherein said recessed part extends in an outward radial direction to an outer recess boundary remote from said main optical axis, said outer recess boundary at least essentially coinciding with said imaginary main lens outer circumference section, and wherein said recess surface essentially only comprises an essentially concave surface section extending along said outer recess boundary and said secondary lens surface extending to said essentially concave surface section.

2. The intraocular lens according to claim 1 wherein said imaginary main lens outer circumference section is at least essentially in a first plane perpendicular to said main optical axis, and said outer recess boundary is at least essentially in a second plane perpendicular to said main optical axis, said first plane at least essentially coinciding with said second plane.

3. The intraocular lens according to claim 1, wherein said recess surface essentially only comprises an essentially concave surface section extending along said outer recess boundary, and said secondary lens surface extending to said essentially concave surface section.

4. The intraocular lens according to claim 3, wherein said concave surface section extends between about 0.2 and 1.2 mm in the radial direction.

5. The intraocular lens according to claim 1, wherein said recessed part in tangential directions is bounded by meridian boundaries extending along meridians of said main lens surface passing through said main optical axis.

6. The intraocular lens according to claim 5, wherein said recessed part extends between 160 and 190 degrees in said tangential directions between said meridian boundaries.

7. The intraocular lens according to claim 1, wherein said secondary lens surface comprises at least two secondary lens surface sections neighbouring in a radial direction, an optical power of one secondary lens surface section being larger in an outward radial direction with respect to a neighbouring secondary lens surface section.

8. The intraocular lens according to claim 1, wherein said lens further comprises a central lens part around said main optical axis, said central lens part fitting within a circle around said main optical axis and having a diameter between 0.1 and 2.0 mm.

9. The intraocular lens according to claim 8, wherein a surface of said central part is adjacent to said main lens surface, defining a main lens inner circumference section of said main lens surface, and adjacent to said recess surface, defining an inner recess boundary of said recess surface.

10. The intraocular lens according to claim 1, wherein said main lens part has an optical power between about −20 and +35 dioptre.

11. The intraocular lens according to claim 1, wherein said secondary lens part has a relative optical power between +0.5 and 10.0 with respect to said main lens part.

12. The intraocular lens according to claim 1, wherein said main lens outer circumference fits within a circle around said main optical axis and having a diameter between 5 and 7 mm.

13. An intraocular lens comprising a posterior side for facing towards the posterior chamber of the human eye, and an anterior side for facing away from the posterior chamber when positioned in the human eye, said anterior side being configured according to claim 1.

14. An intraocular lens comprising a posterior side for facing towards the posterior chamber of the human eye, and an anterior side for facing away from the posterior chamber when positioned in the human eye, said posterior side being configured according to claim 1.

* * * * *